(12) United States Patent
Barbi et al.

(10) Patent No.: US 9,341,585 B2
(45) Date of Patent: May 17, 2016

(54) X-RAY DETECTOR INCLUDING INTEGRATED ELECTRON DETECTOR

(71) Applicant: PULSETOR, LLC, Ringoes, NJ (US)

(72) Inventors: Nicholas C. Barbi, Yardley, PA (US); Richard B. Mott, Ringoes, NJ (US)

(73) Assignee: PulseTor, LLC, Pennington, NJ (US)

( * ) Notice: Subject to any disclaimer, the term of this patent is extended or adjusted under 35 U.S.C. 154(b) by 52 days.

(21) Appl. No.: 14/053,714

(22) Filed: Oct. 15, 2013

(65) Prior Publication Data

US 2014/0042316 A1 Feb. 13, 2014

Related U.S. Application Data

(62) Division of application No. 13/194,611, filed on Jul. 29, 2011, now Pat. No. 8,729,471.

(60) Provisional application No. 61/369,353, filed on Jul. 30, 2010.

(51) Int. Cl.
*G01T 1/20* (2006.01)
*H01J 37/28* (2006.01)
(Continued)

(52) U.S. Cl.
CPC .......... *G01N 23/2257* (2013.01); *G01T 1/2018* (2013.01); *H01J 37/244* (2013.01); *H01J 37/28* (2013.01); *H01J 2237/2443* (2013.01); *H01J 2237/24415* (2013.01)

(58) Field of Classification Search
CPC ....... H01J 37/244; H01J 37/26; H01J 37/261; H01J 37/28; G01T 1/16; G01T 1/00; G01T 1/24; G01T 1/2482; G01T 1/20
USPC ................................................. 250/306–311
See application file for complete search history.

(56) References Cited

U.S. PATENT DOCUMENTS 4,217,495 A  8/1980 Robinson
4,941,980 A  7/1990 Halavee et al.
(Continued)

OTHER PUBLICATIONS

Jones, "Investigation of YAG:Ce Scintillating Fiber Properties Using Silicon Photomultipliers," Dept of Engineering Physics, Air Force Institute of Technology, Mar. 2011 [retrieved on Sep. 29, 2012]. Retrieved from the Internet: URL: http://www.dtic.mil/dtic/tr/fulltext/u2/a538424.pdf—entire document.

(Continued)

*Primary Examiner* — Michael Logie
*Assistant Examiner* — David E Smith
(74) *Attorney, Agent, or Firm* — Eckert Seamans Cherin & Mellott, LLC; Philip E. Levy

(57) ABSTRACT

An X-ray detector includes a housing and an X-ray sensing device provided within the housing along the axis of the housing, wherein the housing is structured to be coupled to the electron column or sample chamber of a charged particle beam device. The X-ray detector also includes an electron detector structured to detect a plurality of electrons ejected from a sample in response to an electron beam impinging on the sample, the electron detector being coupled to the housing on or near the axis such that a first line of sight to the electron detector from a point at which the electron beam impinges on the sample is similar to a second line of sight to the X-ray sensing device from the point at which the electron beam impinges on the sample such that X-ray and Backscattered electron images will show similar parallax and shadowing effects.

40 Claims, 19 Drawing Sheets

(51) Int. Cl.
*G01N 23/225* (2006.01)
*H01J 37/244* (2006.01)

(56) References Cited

U.S. PATENT DOCUMENTS

| | | | |
|---|---|---|---|
| 5,065,020 A | 11/1991 | Kanda | |
| 5,091,650 A | 2/1992 | Uchida et al. | |
| 5,198,675 A | 3/1993 | Hikita et al. | |
| 5,717,206 A | 2/1998 | Watanabe et al. | |
| 5,903,004 A | 5/1999 | Koshihara et al. | |
| 6,811,850 B1 | 11/2004 | Hirata | |
| 6,861,650 B2 | 3/2005 | Kondo et al. | |
| 7,297,914 B2 | 11/2007 | Pang et al. | |
| 7,439,509 B1 | 10/2008 | Grazioso et al. | |
| 7,476,864 B2 | 1/2009 | Baviera et al. | |
| 7,531,812 B2 | 5/2009 | Slowko | |
| 7,626,389 B2 | 12/2009 | Fiedler et al. | |
| 7,635,848 B2 | 12/2009 | Nelson | |
| 7,646,845 B2 | 1/2010 | Lecomte et al. | |
| 7,723,694 B2 | 5/2010 | Frach et al. | |
| 7,750,311 B2 | 7/2010 | Daghighian | |
| 7,812,315 B2 | 10/2010 | Suzuki et al. | |
| 7,924,079 B2 | 4/2011 | Schmand et al. | |
| 2002/0100877 A1* | 8/2002 | Ochiai et al. | 250/489 |
| 2004/0108530 A1 | 6/2004 | Sandvik et al. | |
| 2005/0127294 A1 | 6/2005 | Katane et al. | |
| 2006/0169899 A1 | 8/2006 | Parker et al. | |
| 2006/0243908 A1 | 11/2006 | Shinada et al. | |
| 2006/0255287 A1 | 11/2006 | Cholewa et al. | |
| 2007/0205375 A1 | 9/2007 | Ward et al. | |
| 2008/0155990 A1 | 7/2008 | Gupta et al. | |
| 2008/0308742 A1 | 12/2008 | Gerlach et al. | |
| 2008/0317200 A1 | 12/2008 | Lecomte et al. | |
| 2009/0065704 A1 | 3/2009 | Heringa et al. | |
| 2009/0090866 A1 | 4/2009 | Zhang et al. | |
| 2009/0101817 A1 | 4/2009 | Ohshima et al. | |
| 2009/0296087 A1 | 12/2009 | Dyshkant | |
| 2010/0072365 A1 | 3/2010 | Shoham et al. | |
| 2010/0080351 A1 | 4/2010 | Hession-Kinz et al. | |
| 2010/0198061 A9 | 8/2010 | Daghighian et al. | |
| 2010/0200750 A1* | 8/2010 | Mantz | H01J 37/05 250/310 |
| 2010/0294931 A1* | 11/2010 | Zarchin et al. | 250/310 |
| 2010/0295144 A1 | 11/2010 | Jackson et al. | |
| 2011/0017916 A1 | 1/2011 | Schulz et al. | |
| 2011/0108702 A1 | 5/2011 | Jackson et al. | |
| 2011/0168887 A1* | 7/2011 | Bewick | 250/306 |
| 2011/0204229 A1* | 8/2011 | Schamber | H01J 37/244 250/311 |
| 2011/0248175 A1 | 10/2011 | Frach et al. | |
| 2012/0102435 A1 | 4/2012 | Han et al. | |
| 2012/0160999 A1* | 6/2012 | Zaluzec | H01J 37/244 250/307 |

OTHER PUBLICATIONS

A.G. Stewart et al., Performance of 1-mm2 Silicon Photomultiplier, IEEE Journal of Quantum Electronics, vol. 44, No. 2, Feb. 2008, pp. 157-164.

T.E. Everhart, et al., Wide-band detector for micro-microampere low-energy electron currents, Journal of Scientific Instruments, vol. 37, Jul. 1960, pp. 246-248.

Brian F. Aull et al., Geiger-Mode Avalanche Photodiodes for Three-Dimensional Imaging, Lincoln Laboratory Journal, vol. 13, No. 2, 2002, pp. 335-350.

* cited by examiner

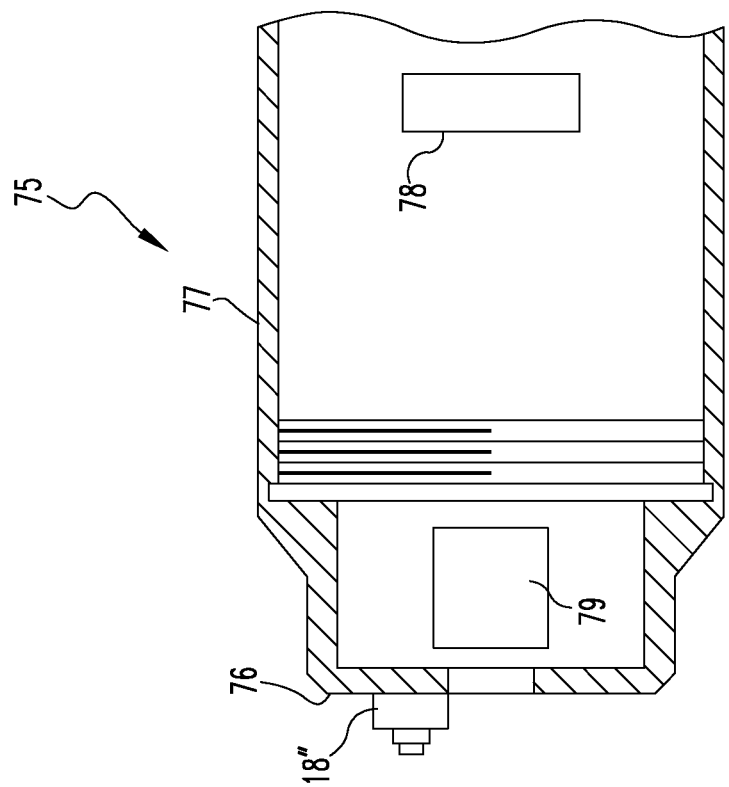
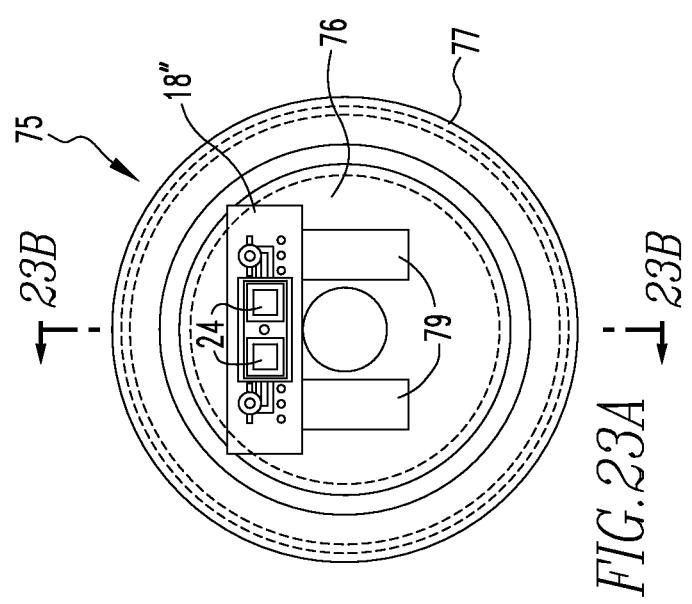

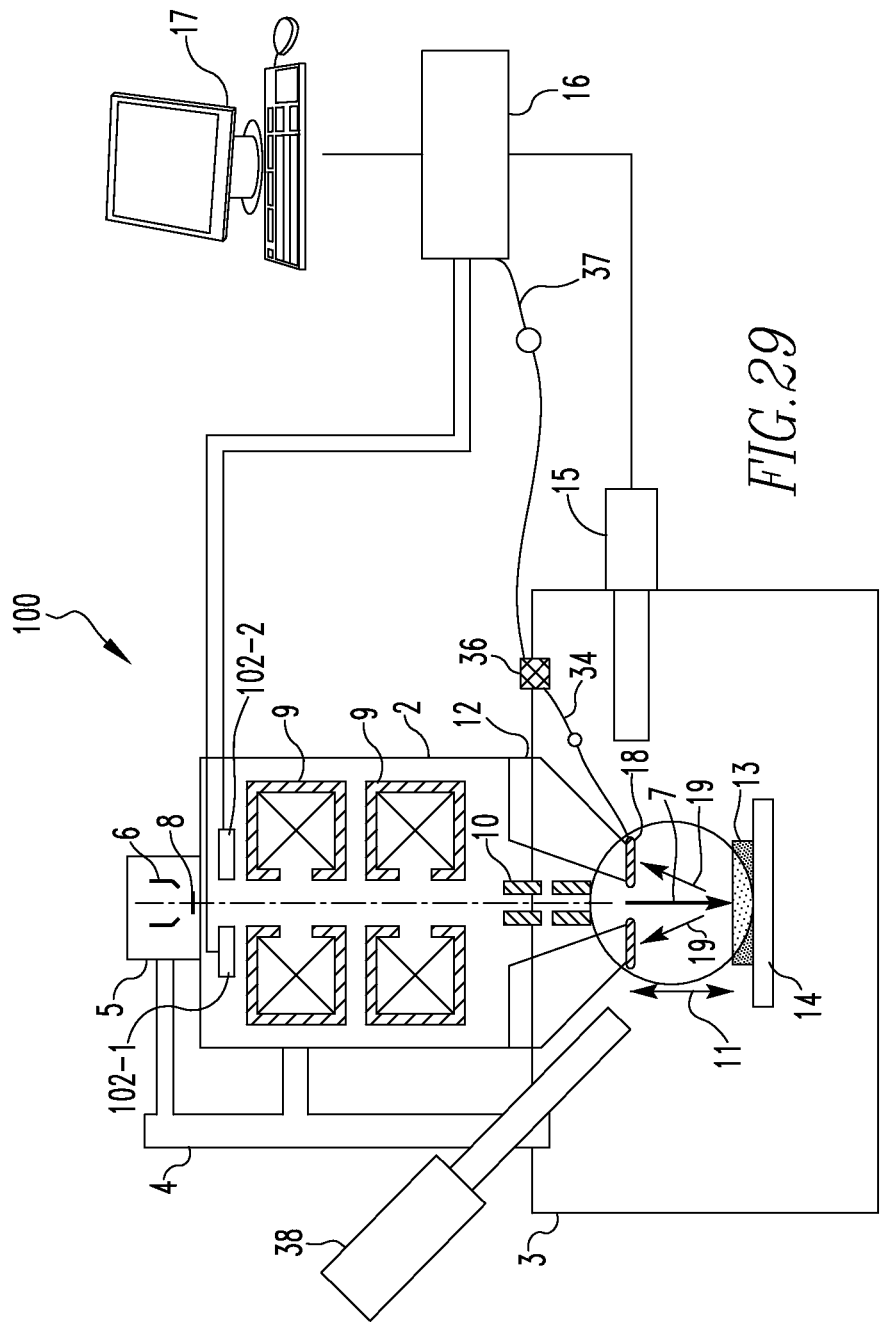

X-RAY DETECTOR INCLUDING INTEGRATED ELECTRON DETECTOR

CROSS-REFERENCE TO RELATED APPLICATIONS

This application is a divisional of co-pending U.S. application Ser. No. 13/194,611, entitled "Electron Detector Including an Intimately Coupled Scintillator-Photomultiplier Combination, And Electron Microscope and X-Ray Detector Employing Same," which was filed on Jul. 29, 2011 and which claims priority under 35 U.S.C. §119(e) from U.S. Provisional Application No. 61/369,353 entitled "Electron Microscope Employing An SiPM Based Electron Detector" and filed on Jul. 30, 2010, the disclosure of which is incorporated herein by reference.

BACKGROUND OF THE INVENTION

1. Field of the Invention

The present invention pertains to electron detection and electron detection devices, and, in particular, to an electron detector including an intimately-coupled scintillator-silicon photomultiplier combination that may be employed in an electron microscope and/or an X-ray detector, such as an X-ray detector used in an electron microscope.

2. Description of the Related Art

An electron microscope (EM) is a type of microscope that uses a particle beam of electrons to illuminate a specimen and produce a magnified image of the specimen. One common type of EM is known as a scanning electron microscope (SEM). An SEM creates images of a specimen by scanning it with a finely focused beam of electrons in a pattern across an area of the specimen, known as a raster pattern. The electrons interact with the atoms that make up the specimen, producing signals that contain information about the specimen's surface topography, composition, and other properties such as crystal orientation and electrical conductivity.

In a typical SEM, a beam of electrons is generated from an electron gun and accelerated to an anode 8 which is held at an accelerating voltage typically between 1 keV and 30 keV, although higher and lower voltage extremes are available on many instruments. The gun is positioned at the beginning of a series of focusing optics and deflection coils, called an electron column or simply "column" because its axis is typically vertical, which in turn is followed by a sample chamber or simply "chamber" housing the sample and accommodating a variety of detectors, probes and manipulators. Because electrons are readily absorbed in air, both the column and chamber are evacuated, although in some cases the sample chamber may be back-filled to a partial pressure of dry nitrogen or some other gas. The electrons may be initially generated by heating a filament, such as Tungsten or LaB6 (thermionic emission), by a strong electrical field (Cold Field Emission), or by a combination of the two (Schottky Emission). The electrons are then accelerated toward an anode, which is maintained at a high voltage called the "accelerating voltage", then follow a path through the electron column, which contains a series of focusing lenses (usually electromagnetic) and scanning coils, such that a finely focused beam of electrons (on the order of 1-10 nanometers) is made to scan in a raster fashion as described above.

A special type of SEM dedicated to elemental analysis using X-rays is called an Electron Probe Micro-Analyzer (EPMA). By definition, the EPMA includes multiple wavelength-dispersive X-ray spectrometers, which employ the principle of X-ray diffraction to sort the X rays emitted from the sample according to their wavelength. Because wavelength spectrometers require a substantial amount of space inside the sample chamber and also require a precise beam-sample-spectrometer geometry, the sample in many EPMAs must be placed at a much longer distance (say 40 mm) from the final lens than in SEMs, sacrificing image resolution to accommodate the improved spectral resolution provided by the wavelength spectrometers.

The first implementation of the electron microscope was the Transmission Electron Microscope (TEM). In this case, an electron beam is generated in a fashion similar to that described for the SEM, and the beam is focused by similar lens arrangements. In the TEM, however, the sample resides within the objective lens field and the transmitted beam passes through one or more projection lenses (also, typically, electromagnetic). The most common TEM image is formed from the primary electrons that pass through the sample, which are influenced by absorption and diffraction. TEMs can provide image resolution on the order of 0.2 nm, several times better than CFE SEMs and more than an order of magnitude better than SEMs based on thermionic emission. Their disadvantages are their cost and the requirement for very small and very thin samples.

There are also instruments that combine some of the features of the SEM and TEM, called Scanning Transmission Electron Microscopes (STEM).

Another instrument which is frequently used in both development and failure analysis in the fields of semiconductor and nanotechnology implements both an electron beam and an ion beam integrated with a single sample chamber such that the electron beam can be used for normal SEM type imaging, while the focused ion beam (FIB) is used for high resolution milling of micro-regions of the sample, without requiring coarse repositioning of the sample. Such an instrument is called a Dual Beam or FIB/SEM. The milling is often used for creating and polishing cross sections in situ, allowing an SEM image of the cross section thus created to be obtained. In this instrument, gas injection systems may also be added, enabling the semiconductor or nano-materials designer, for example, to build or modify structures in situ, using a process conceptually similar to Chemical Vapor Deposition.

When the electron beam hits the specimen in all of these and similar instruments, some of the beam electrons (primary electrons) are reflected/ejected back out of the specimen by elastic scattering resulting from collisions between the primary electrons and the nuclei of the atoms of the specimen. These electrons are known as backscattered electrons (BSEs) and provide both atomic number and topographical information about the specimen. Some other primary electrons will undergo inelastic scattering causing secondary electrons (SEs) to be ejected from a region of the specimen very close to the surface, providing an image with detailed topographical information at the highest resolution. If the sample is sufficiently thin and the incident beam energy sufficiently high, some electrons will pass through the sample (transmitted electrons or TEs). Backscattered and secondary electrons are collected by one or more detectors which are respectively called a backscattered electron detector (BSED) and a secondary electron detector (SED), which each convert the electrons to an electrical signal used to generate images of the specimen. A transmitted electron detector (TED) can be of a similar type or can simply be a screen coated with a long-persistence phosphor.

Most electron detectors used to image BSEs and SEs employ a combination of a scintillator, a light guide (also called a "light pipe") and a photomultiplier tube (PMT), as proposed by Everhart and Thornley (Everhart, T E and R F M Thornley (1960), "Wide-band detector for micro-microampere low-energy electron currents", Journal of Scientific Instruments 37 (7): 246-248). A scintillator is a device made from a material that exhibits scintillation, which is the emission of photons, usually in the visible light, near UV or near IR regions of the spectrum, in response to radiation. An important requirement for scintillators used in scanning electron imaging is that they have a fast decay time, on the order of 100 nanoseconds or less, allowing the image to be recorded with high fidelity (without "smearing") even when very rapid beam scanning rates are used (pixel dwell times on the order of 100 ns or less are available in modern SEMs). This is particularly important in automated image analysis, in which feature size, shape and position must be precisely calculated. Suitable scintillator materials include minerals such as YAG: Ce, YAP:Ce, ZnO:Ga, as well as some plastic scintillators. The scintillator in an electron detector thus generates light (photons) in response to electron impingement thereon. The light guide then collects some fraction of the generated light and transmits it outside the chamber or column to a PMT, which is a vacuum tube device, typically operated at 1000-1500 volts, that detects light. Thus, in such an electron detector, the scintillator emits photons caused by the impingement of BSEs or SEs and the PMT detects the presence of the fraction of photons that are successfully collected and transmitted to it by the light guide. In some references, the light guide, although its use is clearly indicated within detailed descriptions or figures in these references, is not called out specifically, but is assumed to be an integral part of the PMT or scintillator. The light guide and its attachment to the scintillator, however, play an important role in determining the device performance, and its required presence cannot be ignored.

In current electron microscopes, the predominant method of secondary electron detection is the Everhart Thornley (ET) detector just described. Backscattered electron detectors as well are often "ET type" detectors, i.e., the scintillator-light guide-PMT sequence is used, but the manner in which the light guide is attached to the scintillator differs significantly in the two applications, as further described below. The PMT of the BSED, the SED and the TED reside outside of the vacuum chamber of the EM because a PMT is a rather large, rigid device having a size on the order of several centimeters in all directions. As a result, each such electron detector is comprised of a scintillator positioned inside the vacuum chamber and a light pipe or similar light transporting device to carry a fraction of the generated photons out to a PMT residing outside the vacuum chamber through a chamber access port.

A typical SEM sample chamber will have a limited number of access ports available to accommodate accessory instruments or tools, such as one or more energy dispersive X-ray detectors, a wavelength dispersive X-ray spectrometer, an electron backscatter diffraction device, a cathodoluminescence spectrometer, micromanipulators, and, when laser or ion beam sources are available, a secondary ion mass spectrometer or a Raman spectrometer. These accessories, however, compete for port availability with the PMTs from the electron detectors, which may be several in number, including an SED, BSED, Low-Vacuum SED, and possibly a TED. If all the PMTs in an SEM could be eliminated, an equal number of ports would be made available for the mounting of additional important analytical tools that would otherwise be excluded from exploitation.

The SED and BSED differ as a result of the difference in the energy of the electrons detected. SEs are very low in energy, defined as 50 eV or less, and are drawn to the detector by a bias voltage of a few hundred volts and are then further accelerated to a scintillator biased with several thousand volts. The ability to influence the trajectory of SEs through a relatively low bias voltage enables the detector to be positioned to the side of the sample. BSEs have higher energy than SEs, with most BSEs having energy at or near the accelerating voltage of the primary beam, and their trajectory cannot be influenced by a voltage sufficiently low so as not to impact the primary beam. BSE imaging is therefore line-of-sight. Furthermore, when electron incidence is normal to the sample surface, which is typical, the distribution of BSEs in the space above the sample follows a cosine law, in which most of the electrons are backscattered along or near the axis of the electron column. These factors require that the BSED be placed immediately below the pole piece of the objective lens, in an annular fashion, such that the primary beam can pass through a small hole (e.g., 5 mm in diameter) in the center of the BSED. In order to achieve the highest image resolution in an SEM, samples must be placed as close as possible to the pole piece of the objective or "final" lens, i.e., samples should be imaged at the shortest possible "working distance". A short working distance requires a short lens focal length, which in turn dictates a high lens current, minimizing aberrations and improving resolution. Therefore, the portion of the BSED which occupies space between the sample and the final lens pole piece, namely the scintillator and its attachment to the light pipe, must be as thin as possible. An important implication of this requirement in a scintillator-light guide combination is that the photons emitted from the scintillator can be collected only through the edge of the scintillator disc, as space above the scintillator cannot be sacrificed to accommodate the optics which would be required to redirect the photons into the light guide. The light guide in such assemblies is therefore coupled only to the periphery of the scintillator, through a C-shape coupling which grasps the disc by its thickness, not to its back surface (the surface opposite the surface on which the electrons impinge the scintillator). This results in a significant reduction in light collection efficiency for otherwise optimum BSED geometries. A further implication is that the light generated on the side of the scintillator disk opposite the light guide is not effectively transmitted to the PMT, meaning that there is always a topographical bias in the image (the view from one side of the column centerline dominates the image). In comparison, in ET detectors used as SEDs, the back-side of the scintillator disc is bonded directly to a mating surface of the light guide as there are no such geometrical and space restrictions.

A second type of BSED uses photodiodes also placed symmetrically around the centerline of the column, just under the pole piece of the final lens. The advantage of such a detector is that discrete photodiodes can be arranged around the column centerline, in "sectors", and the signal collected from one or more of the sectors can be used to form the image. If sectors on one side only of the centerline are used to form the image, topographical contrast will dominate; if all of the sectors are used, topography will be eliminated and the image will be dominated by compositional contrast. In spite of this important capability, scintillator-based devices are often chosen over segmented photodiode detectors because they have much higher gain and can image at much faster scanning rates; in this case, the advantage of the selection of topographic or compositional modes provided by the photodiode detector is lost.

A third (and the least common) type of electron detector is a micro-channel plate (MCP) which, unlike the ET detectors, can be entirely contained inside the SEM, eliminating the need for a mounting port. The MCP, however, requires vacuum levels <$10^{-6}$ torr, one or two orders of magnitude better than is typical inside the specimen chamber of the SEM. Furthermore, the MCP is slow and shares the disadvantage with the photodiode detector that it is unable to keep pace with the very short dwell times (high scanning rates) used in modern SEMs.

There is thus a great, unsolved need for an electron detector technology that is small, operates at low voltage, can be used inside the column or sample chamber, allows segmentation and high gain simultaneously, can be used in multiple, unique locations and indeed be positioned in situ via external manual or software control, and allows the number of access ports of an SEM that may be utilized for other analytical tools (and not electron detection) to be increased. There also accrue significant benefits in eliminating the requirement for a light guide, specifically the decreasing cost and complexity and increasing efficiency.

SUMMARY OF THE INVENTION

In one embodiment, a charged particle beam device, such as an electron microscope, is provided that includes an electron source structured to generate an electron beam, the electron source being coupled to an electron column, the electron column at least partially housing a system structured to direct the electron beam toward a specimen positioned in a sample chamber to which the electron column is coupled, and an electron detector. The electron detector includes one or more assemblies positioned within the electron column or the sample chamber, each of the assemblies including an SiPM and a scintillator directly connected face-to-face to an active light sensing surface of the SiPM without a light transporting device being positioned in between the scintillator and the SiPM, wherein in each of the one or more assemblies the scintillator is structured to emit photons when impinged by electrons ejected from the specimen in response to the electron beam impinging on the specimen and the SiPM is structured to generate a signal responsive to receipt of the photons from the scintillator.

In another embodiment, a method of producing an image of a specimen positioned within a sample chamber coupled to an electron column of a charged particle beam device is provided. The method includes generating an electron beam, directing the electron beam through the electron column and toward the specimen, wherein a plurality electrons are ejected from the specimen in response to the electron beam impinging on the specimen, and generating a signal proportional to an intensity of the plurality electrons using an electron detector. The electron detector includes an assembly positioned within the electron column or the sample chamber, the assembly including an SiPM and a scintillator directly connected, face to face, to an active light sensing surface of the SiPM without a light transporting device being positioned in between the scintillator and the SiPM, wherein the electrons impinge on the scintillator and in response thereto the scintillator emits a plurality of photons and wherein the SiPM generates the signal responsive to receipt of the plurality of photons from the scintillator. Finally, the method further includes generating the image of the specimen based on the signal.

In another embodiment, a charged particle beam device is provided that includes an electron source structured to generate an electron beam, the electron source being coupled to an electron column, the electron column at least partially housing a system structured to direct the electron beam toward a specimen held on a specimen holder within a sample chamber coupled to the electron column, the system including a final lens, and a backscattered electron detector. The backscattered electron detector includes an assembly positioned in between a bottom of the final lens and the specimen holder, the assembly including a scintillator and an SiPM, the scintillator having a front surface and a back surface opposite the front surface, the front surface facing the specimen holder and being positioned to receive a plurality of electrons ejected from the specimen in response to the electron beam impinging on the specimen, the back surface of the scintillator being directly connected, face to face, to an active light sensing surface of the SiPM without a light transporting device being positioned in between the scintillator and the SiPM, wherein the scintillator is structured to emit a plurality of photons from the back surface when the plurality of electrons impinge on the front surface and wherein the SiPM is structured to generate a signal responsive to receipt of the plurality of photons from the scintillator.

In still another embodiment, a method of producing an image of a specimen positioned on a specimen holder within a sample chamber coupled to an electron column of a charged particle device is provided. The method includes generating an electron beam, directing the electron beam through the electron column and toward the specimen using a system including an final lens, wherein a plurality of electrons are backscattered from the specimen in response to the electron beam impinging on the specimen, and generating a signal proportional to an intensity of the plurality electrons using an electron detector. The electron detector including an assembly positioned in between a bottom of the final lens and the specimen holder, the assembly including a scintillator and an SiPM, the scintillator having a front surface and a back surface opposite the front surface, the front surface facing the specimen holder and being positioned to receive the plurality electrons, the back surface of the scintillator being directly connected, face to face, to an active light sensing surface of the SiPM without a light transporting device being positioned in between the scintillator and the SiPM, wherein the plurality of electrons impinge on the front surface of the scintillator and in response thereto the scintillator emits a plurality of photons from the back surface and wherein the SiPM generates the signal responsive to receipt of the plurality of photons from the scintillator. Finally, the method includes generating the image of the specimen based on the signal.

In yet another embodiment, an X-ray detector is provided that includes a housing, an X-ray sensing device provided within the housing, and an electron detector structured to detect a plurality of electrons, the electron detector being coupled to the housing and including one or more SiPMs, each of the one or more SiPMs being structured to generate a signal responsive to certain ones of the electrons.

In still another embodiment, a method of detecting electrons and X-rays using an X-ray detector including a housing and an X-ray sensing device provided within the housing is provided. The method includes detecting one or more X-rays that enter the housing the X-ray sensing device, and detecting the plurality of electrons using an electron detector coupled to the housing, the electron detector including one or more SiPMs.

Another embodiment provides a method of producing an image of a specimen positioned within a sample chamber coupled to an electron column of a charged particle beam device that includes generating an electron beam, directing the electron beam through the electron column and toward the specimen, wherein a plurality electrons are ejected from the specimen in response to the electron beam impinging on the specimen, and directly detecting the plurality electrons using an electron detector device without using a scintillator. The electron detector device includes an array of independent detecting elements connected in parallel on a substrate, each detecting element comprising an avalanche photodiode, the electron detector being structured to allow substantially all electrons incident on the electron detector device to impinge on the detecting elements rather than being structured to absorb substantially all electrons incident on the electron detector device. The method further includes generating and outputting from the electron detector a signal proportional to an intensity of the plurality electrons responsive to the directly detecting the plurality electrons, and generating the image of the specimen based on the signal.

A charged particle beam device is provided in yet another embodiment that includes an electron source structured to generate an electron beam, the electron source being coupled to an electron column, the electron column at least partially housing a system structured to direct the electron beam toward a specimen positioned in a sample chamber to which the electron column is coupled, and an electron detector device positioned within the electron column or the sample chamber, the electron detector device being structured to detect a plurality electrons ejected from the specimen in response to the electron beam impinging on the specimen without using a scintillator, the electron detector device including an array of independent detecting elements connected in parallel on a substrate, each detecting element comprising an avalanche photodiode, the electron detector device being structured to allow substantially all electrons incident on the electron detector to impinge on the detecting elements rather than being structured to absorb substantially all electrons incident on the electron detector device.

In still another embodiment, a scanning electron microscope system is provided that includes a housing including an electron column and a sample chamber coupled to the electron housing, an electron source coupled to the electron column and structured to generate an electron beam, wherein the electron column has a column axis along which the electron beam is directed, and a system provided within the housing and structured to direct the electron beam toward a specimen. The scanning electron microscope system also includes a first electron detector structured to detect a first plurality of electrons ejected from the specimen in response to the electron beam impinging on the specimen, the first electron detector including one or more first SiPMs positioned within the housing on a first side of the column axis, each of the one or more first SiPMs being structured to generate a respective first signal responsive to certain first ones of the electrons ejected from the specimen and a second electron detector structured to detect a second plurality of electrons ejected from the specimen in response to the electron beam impinging on the specimen, the second electron detector including one or more second SiPMs positioned within the housing on a second side of the column axis, each of the one or more second SiPMs being structured to generate a respective second signal responsive to certain second ones of the electrons ejected from the specimen. Finally, the system includes a display device and electronic circuitry structured to (i) generate a first image signal based on each first signal, (ii) generate a second image signal based on each second signal, the first image signal being offset angularly from the second image signal, and (iii) cause an image to be displayed by the display device by causing the first and second image signals to be displayed alternately on the display device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 23A is a front elevational view and FIG. 23B is a cross-sectional view taken along lines 23B-23B of FIG. 23A that show one implementation of a combined EDX-BSED system according to another embodiment of the present invention;

FIG. 29 is a schematic diagram of an SEM according to an alternative exemplary embodiment of the present invention.

DETAILED DESCRIPTION OF EXEMPLARY EMBODIMENTS

Figure 1:
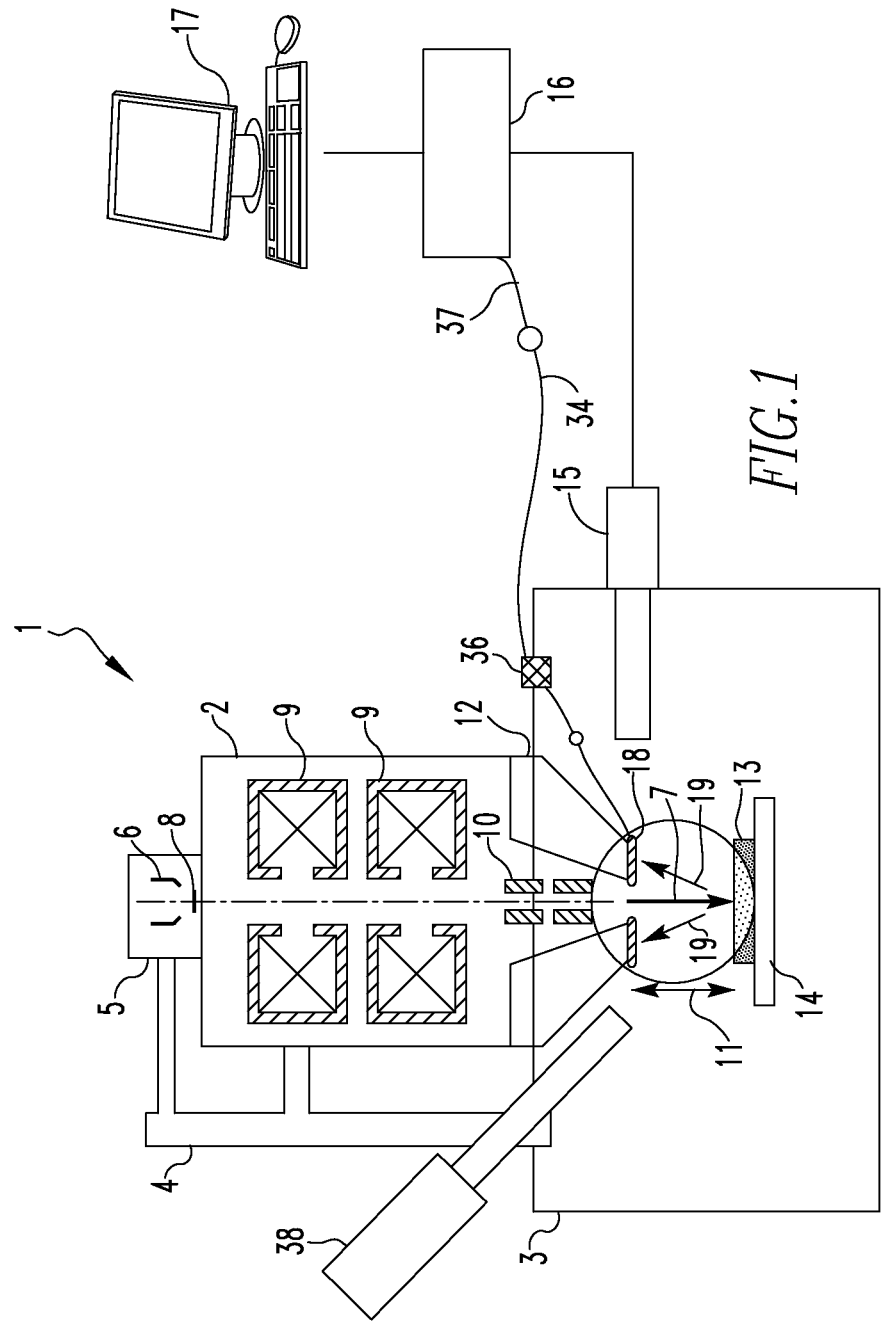
FIG. 1 is a schematic diagram of an SEM according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly connected" means that two elements are either directly in contact with each other or are connected to one another by a bonding/coupling material or agent without any other intermediate elements, parts or components in between. As used herein, "fixedly coupled" or "fixed" means that two components are coupled so as to move as one while maintaining a constant orientation relative to each other. As used herein, the statement that a first item is "based on" a second item shall mean that the second item serves as a direct or indirect (such as through one or more intermediate calculations and/or conversions) basis for the first item (either alone or in conjunction with one or more additional items, i.e., the first item may be based on the second item alone or on the second item and a third item).

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of an SEM 1 according to one exemplary embodiment of the present invention. SEM 1 includes an electron column 2, normally positioned vertically, coupled to a sample chamber 3. Electron column 2 and sample chamber 3 may at times herein be referred to collectively as an evacuated housing, being evacuated through a pumping manifold 4. In some cases, the sample chamber 3 may be referred to simply as the "chamber" and the electron column simply as the "column"; when either one is referred to singly, it may also apply to the entire evacuated housing. An electron gun assembly 5 comprising an electron source 6 is provided at the top of column 2. Electron source 6 is structured to generate an electron beam 7 within column 2, which beam continues on its path into sample chamber 3, directed toward and eventually impinging on the sample (or specimen) 13. SEM 1 further includes one or more condenser lenses 9 within column 2 which focus the beam 7 of primary electrons, also called the "primary beam", to a predetermined diameter, such that the beam intensity, i.e., the "probe current", increases strongly with the beam diameter. The column 2 of SEM 1 also includes deflection (scanning) coils 10 and an objective lens 12, represented by its pole piece, which further focuses the electron beam 7 to a small diameter, such that the electron beam 7 is convergent on the sample 13 at the selected working distance 11 (i.e., the distance between the bottom of the pole piece of the objective lens 12 and the surface of the sample 13), such sample 13 being positionable in several axes (usually X-Y-Z-Tilt-Rotation), by virtue of a sample stage (or specimen holder) 14. Scanning coils 10 deflect the electron beam 7 and create the raster scan in the X-Y axis on the surface of sample 13. In the illustrated embodiment, there is also at least one ET detector, such as SED detector 15, entering the sample chamber 3 or the column 2 through an access port, such detector 15 providing electrical signals to a control system 16 (comprising suitable electronic processing circuitry), which in turn produces a secondary electron image on a display system 17.

An electron detector 18 according to one exemplary embodiment of the present invention is positioned under the pole piece of the objective lens 12 within sample chamber 3. Electron detector 18 in the exemplary embodiment is structured to detect electrons 19 which are backscattered from the sample 13 positioned within sample chamber 3 on sample stage 14. However, as described elsewhere herein, electron detector 18 may also be optimized and/or positioned to monitor secondary electrons generated from sample 13. Electron detector 18 employs at least one Scintillator-SiPM coupled pair assembly 24 (FIG. 2), which is for detecting the electrons. The electron detector 18 and the region immediately surrounding it, as identified by the dotted outline in FIG. 1, is expanded schematically in FIG. 2.

Figure 2:
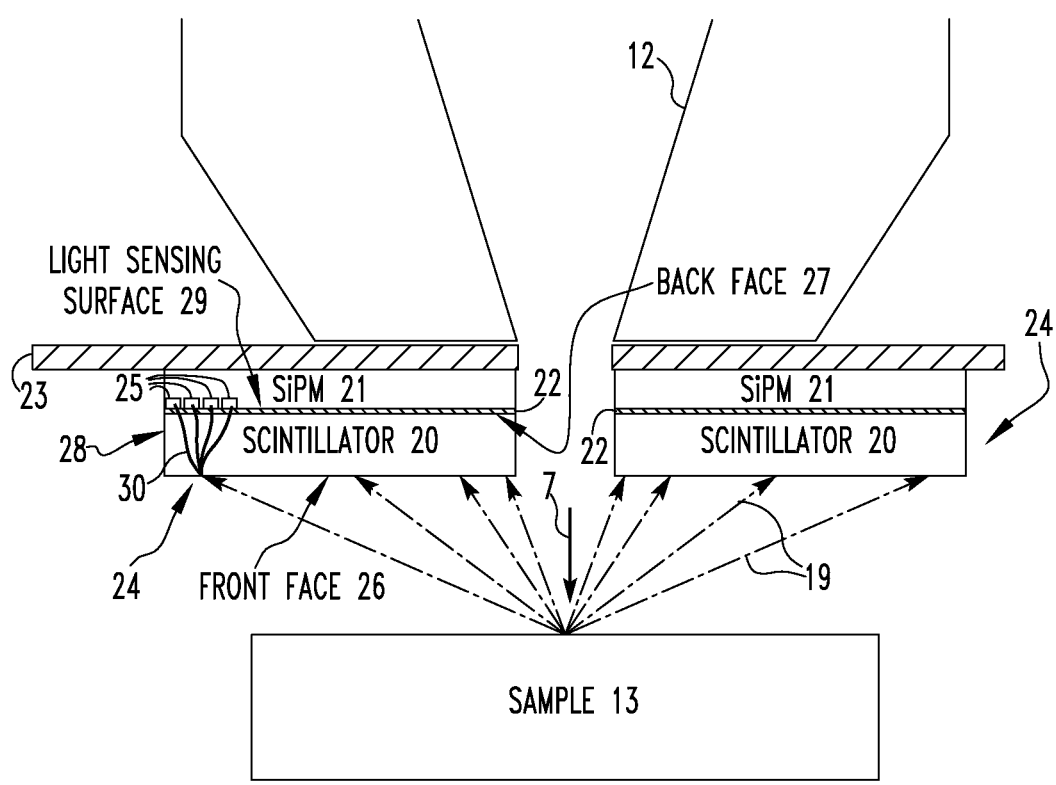
FIG. 2 is a schematic diagram of portion of the SEM of FIG. 1 showing an exemplary embodiment of a scintillator-SiPM coupled pair assembly forming a part of an electronic detector of the SEM of FIG. 1.

Referring to FIG. 2, in the exemplary embodiment, the Scintillator—SiPM coupled pair assembly 24 includes a scintillator 20 that, as described in detail below, is directly connected to at least one silicon photomultiplier (SiPM) 21 by a light transmitting adhesive agent 22, such as an optical glue, an immersion oil or another similar coupling agent. The adhesive agent 22 is chosen such that it has a high transmittance for the emission region of the scintillator 20, and such that the refractive index matches the substrates as closely as possible to minimize Fresnel reflection losses. Scintillator 20 may be any suitable scintillator, such as, without limitation, a Yttrium Aluminum Garnet (YAG), Yttrium Aluminum Perovskite (YAP), ZnO, SnO2, or ZnS based material or a plastic scintillator. In the exemplary embodiment, scintillator 20 is a YAG:Ce scintillator and EPI Optocast 3553-HM is selected as the light transmitting adhesive agent 22.

As seen in FIG. 2, scintillator 20 includes a front face 26 and an opposite back face 27, as seen from the view point of the surface of sample 13. In the exemplary, non-limiting embodiment, scintillator 20 is a rectangular cuboid having side surfaces (edges) 28, although other scintillator geometries are also possible. As illustrated in FIG. 2, the Scintillator-SiPM coupled pair assembly 18 is, in the exemplary embodiment, configured such that electrons (e.g., backscattered electrons) impinge on the front face 26 of scintillator 20. As is known in the art, SiPM 21 is a solid state device that can detect light flashes made of a few photons with a single photon resolution. SiPM 21 consists of an array of several hundred to thousands of small, identical and independent detecting elements 25, commonly known as microcells, each typically square and tens of microns on a side, connected in parallel on a common single silicon substrate of typical wafer thickness, e.g. 450 microns, an example of such a device being shown in FIG. 3. The detecting elements 25 form a light sensing surface 29 of SiPM 21 (FIG. 2). Each detecting element/microcell 25 is, in the exemplary embodiment, a passive-quenched Geiger-mode avalanche photodiode (APD) lithographically produced on the silicon substrate. Each side of the typically square microcell 25 is on the order of 25-100 microns. A smaller microcell size enables a higher density of microcells, which in turn provides a wider dynamic range (higher count rates can be measured at a given bias voltage); the increased number of microcells, however, means more "dead space" surrounding the microcells in their interstices, and therefore, a lower "fill factor" (the percentage of the active area of the device that actually is light sensitive) and consequently lower efficiency. For a 50 micron microcell size, the density is $400/mm^2$ with a fill factor of 0.5; SiPMs using 25 micron cells are currently being made with a density of $1600/mm^2$. Each microcell 25 is connected in parallel to other microcells 25 through a large series polysilicon resistor 33 (FIG. 3) integrated within the lithography. FIG. 4 is a more generalized schematic diagram of a microcell 25 according to an exemplary embodiment, showing the anti-reflective coating layer 32, the metal contact 33, the $SiO_2$ layer 35, the guard ring 37 and the metal contact 39 thereof.

Although each SiPM manufacturer will have a unique design, shallow junction technology (meaning that the SiPM devices have a shallow n+ on p junction) imparts a high quantum efficiency in the blue region of the light spectrum, in addition to the normal high sensitivity to the green light emission such as is characteristic of the YAG:Ce scintillator. This SJ-SiPM technology allows scintillators with shorter decay times than that of YAG:Ce to be used in Scintillator-SiPM coupled pair assemblies 24 as described herein, which will ultimately be needed to provide such devices that are able to keep pace with the shortest electron beam dwell times. Such short dwell times are needed for beam-sensitive samples and to increase throughput when fast, automated feature analysis is required. The YAG:Ce scintillator, which emits near the 550 nm wavelength (green light) has a recovery time reported to be on the order of 80 nsec; the YAP:Ce (Ce-doped Yttrium Aluminum Perovskite) scintillator, which emits in the 385 nm wavelength range (toward the violet region of the spectrum and near UV) has been reported to be on the order of 20 nsec; and the ZnO:Ga scintillator, which emits in a region similar to YAP:Ce, has been reported to be 2 nsec, an order of magnitude faster than YAP. Use of YAP or ZnO scintillators in conventional ET detectors may be problematic, because the emission wavelength around 400 nm requires that light guides be made of quartz rather than the more flexible acrylic, the latter being generally preferred by most detector designers.

SiPMs were developed in the 1990s, predominantly in Russia for photon counting applications (B. Dolgoshein, et al, "Nuclear Instruments and Methods in Physics Research" A 563 (2006) 368-376). SiPMs are solid state, small, low voltage (tens of volts compared to hundreds or thousands of volts for the PMT) devices and are insensitive to magnetic fields. Recent renewed interest in the development of these devices has been motivated by the need for an electron multiplication technique that is insensitive to magnetic fields for use in combination Proton Emission Tomography (PET) and Magnetic Resonance Imaging (MRI) instruments.

The use of SiPMs as imaging devices in electron microscopy was not, however, prior to the present invention, considered by developers in either the field of photon counting device development and medical imaging or the field of electron microscopy. The advantages of SiPMs over PMTs in medical imaging devices, where single photon counting is both the requirement and the focus of development in the field, did not extrapolate to the development of scintillator-SiPM coupled pairs for use as small, low voltage, fast, mobile and efficient electron detection devices in the electron microscope.

Figure 5:
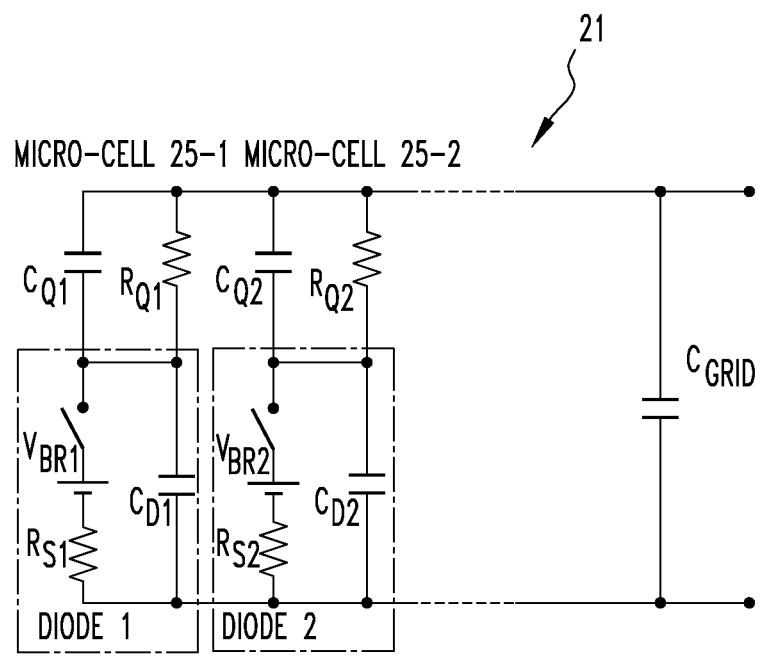
FIG. 5 is a schematic circuit diagram of the SiPM of the scintillator-SiPM coupled pair assembly of FIG. 2 according to one embodiment that shows a plurality of microcells of the SiPM.
Figure 6A:
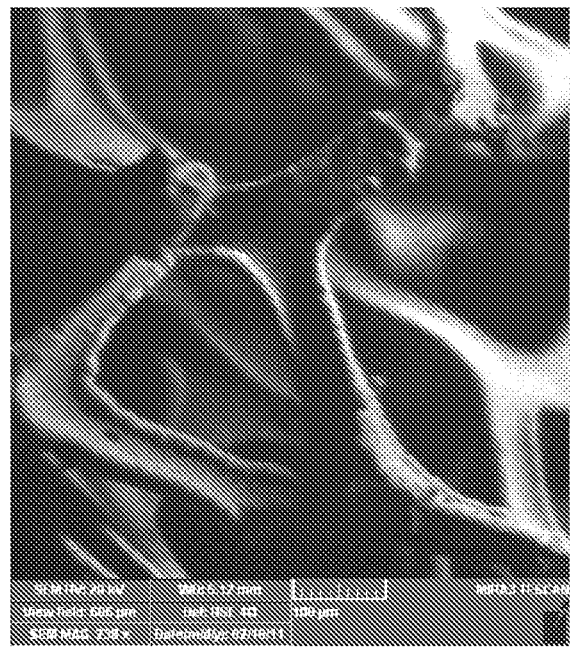
FIGS. 6A and 6B are computer illustrated images collected using an embodiment of an electron detector as shown in FIGS. 1 and 2 at 100 and 500 nsec per pixel, respectively.
Figure 6B:
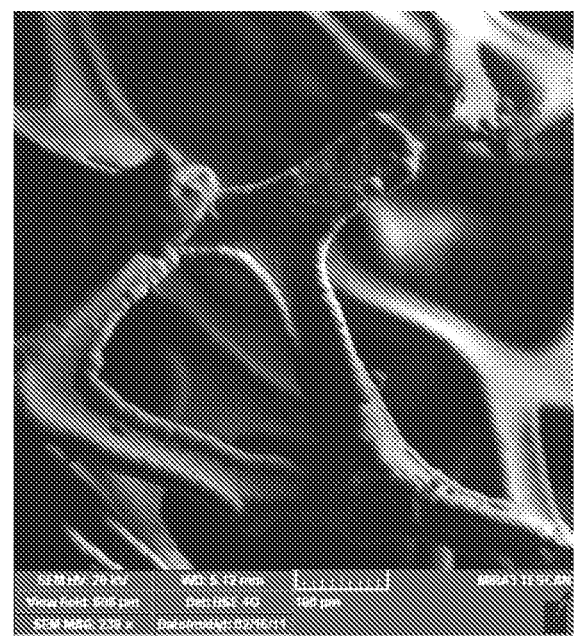

SiPMs are intrinsically fast devices due to the very small width of the depletion region and the extremely short Geiger type discharge, having recovery times on the order of 100 ns. The single cell pulse decay time is further determined by the value of the quench resistor and the capacitance of the cell (see FIG. 5, which is a schematic circuit diagram of an SiPM 21 showing a plurality of microcells 25). The dependence on the quench resistor gives one possible direction to increasing the speed of the SiPM still further. Compared to PMTs, they are much smaller, more robust, require only low voltage to operate, and are positionable in-situ using micromanipulators or some other appropriate mechanical positioning mechanism. As stated earlier, another possible source of improvement in the speed of the Scintillator-SiPM coupled pair assembly 24 is the use of faster scintillators. Initial tests, however, show that even the current electron detector 18 having a Scintillator-SiPM coupled pair assembly 24 as described herein wherein an SiPM 21 is directly coupled with a YAG:Ce scintillator 20, is capable of providing images at very fast scanning rates. FIGS. 6A and 6B are computer illustrated images collected using an electron detector 18 at 100 and 500 nsec per pixel, respectively (HV 20 kV, beam current 9.7 nA, WD 5 mm).

Furthermore, compared to bulk photodiodes, SiPMs are much faster, able to keep pace with dwell times on the order of 100 nsec per pixel. Compared to MCPs, they are have the aforementioned speed advantage and can operate in poor vacuum environments or even in air.

It is known that large area single Avalanche Photodiodes (APDs) can be used for BSE imaging when used in the proportional mode, i.e., at a relatively high voltage close to but below the breakdown voltage of the device. When energetic electrons are absorbed in the detector, they create electron hole pairs, producing an output current that in turn is used to modulate the brightness of a display. The relatively high reverse bias sufficiently accelerates the generated electrons (but not the holes) such they can themselves cause impact ionizations, resulting in a small avalanche. In this mode, the APD has a gain between 10 and a few hundred, while still maintaining the proportionality between the number of incident events and the output current of the device and, in turn, the image brightness on the display. However, the large device size and its associated capacitance, as well as the requirement for subsequent integrating electronics, make the device relatively slow and, therefore, unusable at the short dwell times of modern SEMs (which are often operated at dwell times of 100-500 nsec per pixel, with ultimate speeds being in the range of 20-50 nsec per pixel).

If the APD is used in a limited Geiger mode, i.e., operated at 10-25% above the breakdown voltage, it is called an SPAD (for Single Photon Avalanche photodiode). In this operational mode, both the generated electrons and holes have sufficient energy to produce subsequent ionization, and a self-propagating chain reaction occurs. A much higher gain, about $10^6$, is realized. In this mode, however, a single event causes a full avalanche, i.e., saturation in the device. The current resulting from a single event in the device is the same as that resulting from multiple events. As a result, the device becomes binary and cannot produce a useful image. According to Aull et al, "Geiger-Mode Avalanche Photodiodes for Three-Dimensional Imaging," Lincoln Laboratory Journal, Volume 13, Number 2, 2002, in order to shut off (or "quench") the avalanche so that the APD is ready to detect another event, the APD is either "passively" or "actively" quenched. In passive quenching (as in the schematic drawing of FIG. 5), as stated in Aull et al., the device "is charged up to some bias above breakdown and then left open circuited. Once the APD has turned on, it discharges its own capacitance until it is no longer above the breakdown voltage, at which point the avalanche dies out. An active-quenching circuit senses when the APD starts to self-discharge, and then quickly discharges it to below breakdown with a shunting switch. After sufficient time to quench the avalanche, it then recharges the APD quickly by using a switch."

Figure 3:
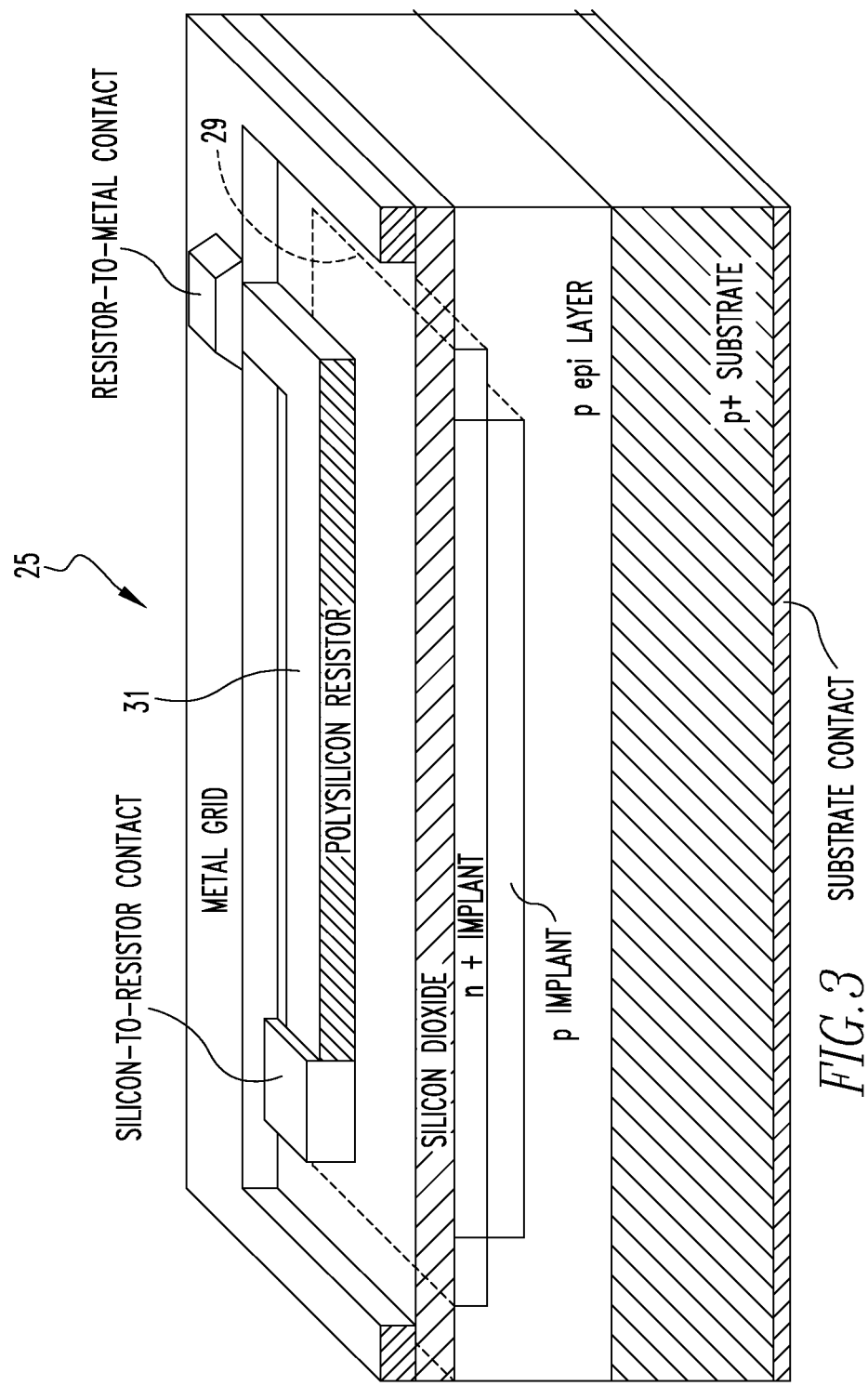
FIGS. 3 and 4 are schematic diagrams of exemplary microcells that may form a part of the SiPM of the scintillator-SiPM coupled pair assembly of FIG. 2.
Figure 4:
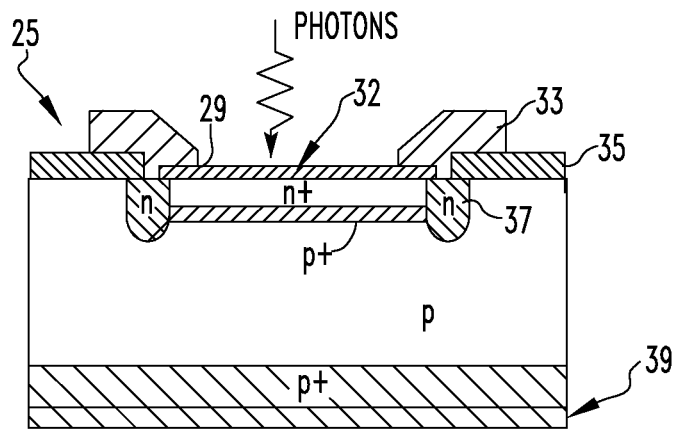

As discussed elsewhere herein, an SiPM, such as SiPM 21, is a lithographically produced device which includes multiple SPAD microcells 25 operated in limited Geiger mode, each microcell 25 typically being 25-100 microns square, on a single silicon substrate, each with its own passive quenching resistor (FIGS. 3 and 4). A typical device using 50 micron cells from one manufacturer will have a cell density of 400/mm$^2$, while devices with 25 micron cells will have a density of 1600/mm$^2$. Each cell works precisely as described above for the passively quenched discrete device. However, in the SiPM, one event will trigger an avalanche in one cell, while a simultaneous event will trigger an avalanche in another; the outputs of all the cells are summed together.

Figure 7:
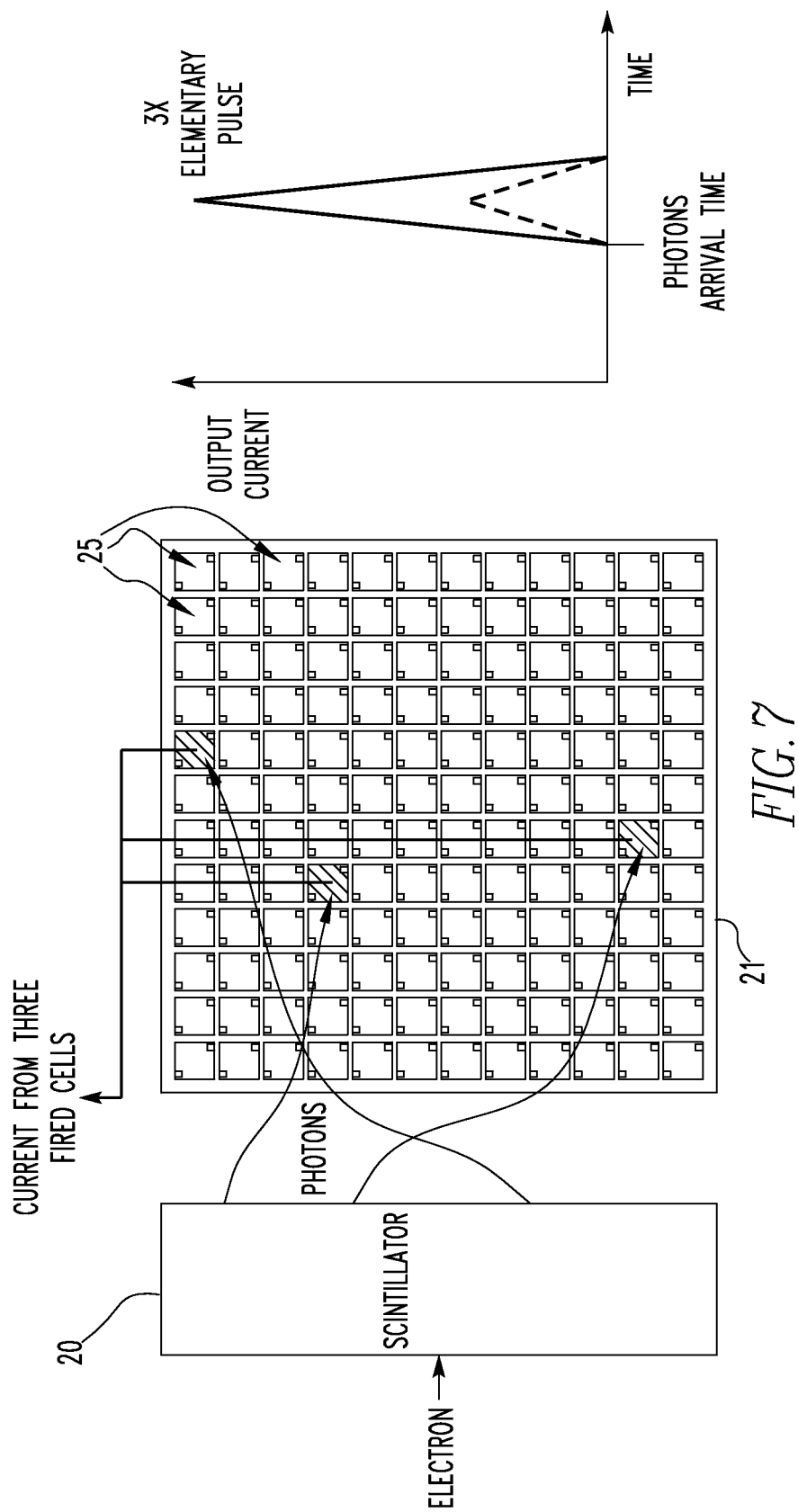
FIG. 7 is a schematic diagram illustrating the operation of the SiPM of the scintillator-SiPM coupled pair assembly of FIG. 2 according to one embodiment.

Referring again to FIG. 2, when a single backscattered electron of the plurality of backscattered electrons 19 strikes the scintillator 20, multiple photons 30 are produced. In turn, each photon 30 directed toward the SiPM 21 is likely to strike a different microcell 25 of SiPM 21, generating a single electron-hole pair. Each of the carriers, i.e., the electron and the hole, has sufficient energy to create its own electron hole pairs, resulting in an avalanche, which multiplies the single carrier generated by the photon 30 by a factor on the order of one million within each microcell 25. The current produced by an avalanche in the microcell 25 is independent of the energy of the photon 30 and is the quantum of charge generated by the sensor. If n photons 30 reach the SiPM 21, the above-mentioned mechanism takes place in each microcell 25 hit by a photon 30. The charge delivered by the sensor is now n times the quantum packet. Exploiting this mechanism, the output signal of SiPM 21 is proportional to the light intensity with a single photon resolution. This process is illustrated in FIG. 7.

In this way, the gain of an APD operated in limited Geiger mode (SPAD) is realized, while at the same time maintaining the proportionality of device output current to the number of incident events. Each microcell 25 operates as a binary device but the SiPM 21 itself is an analogue detector. The number of cells that fire is proportional to the number of incident events until the event intensity is so high that all cells fire and saturation is reached. The dynamic range is intrinsically high because of the large number of microcells 25, but can be increased by using a higher density of smaller microcells 25 at the expense of efficiency. In practice, if saturation is reached, the primary electron beam current can be reduced, which has the corresponding advantage of increasing image resolution.

Silicon Photomultipliers are also known as Multi-pixel photon detectors (MPPD), Multi-Pixel photon counters (MPPC), Multi-Pixel Avalanche Photodiodes (MAPD), and a variety of other names.

As seen in FIG. 2, in the exemplary configuration, the back face 26 of scintillator 20 is directly connected to light sensing surface 29 of SiPM 21 by the light transmitting adhesive agent 22. Thus, light that is generated by scintillator 20 in response to electrons impinging on front face 26 in the direction of back face 27 will be incident on the light sensing surface 29 of the SiPM 21. As noted elsewhere herein, SiPMs are relatively small devices, from 1 mm square to 1 cm square and about 0.5 mm thick. In addition, scintillator 20 may be made of approximately matching area with a thickness ranging from 0.5 mm to 50 microns. The Scintillator-SiPM coupled pair assembly 24, therefore, can be mounted on a thin PCB 23, to produce a device with a total thickness of a few mm. As a result, Scintillator-SiPM coupled pair assembly 24 may be made to be a thin device able to fit within the region between the sample 13 and the objective lens 12 (the "final lens") in an EM such as SEM 1 and still retain the ability to use the short working distance 11. An important characteristic of this unique capability is that the light from the scintillator 20 is transmitted more efficiently by the direct face to face contact with the SIPM 21 than the through-the-edge technique required with conventional Scintillator-light guide combinations of the prior art.

Referring again to FIG. 1, electron detector 18 (which in the exemplary embodiment is a BSED) is coupled to control system 16 by wires 34 (e.g., bias, signal, and ground wires) which pass through a vacuum feed-through 36 provided in sample chamber 3. Vacuum feed-through 36 can be very small and placed in a part of sample chamber 3 (or, alternatively, column 2) that is unusable for mounting the other types of detectors and/or beam sources described herein. When electron beam 7 of SEM 1 strikes a micro-region of specimen 13, electrons are both emitted (SEs) and backscattered (BSEs) from that location. For a given primary beam current and voltage, the intensity of the electrons is dependent upon topography and elemental composition, among other factors. As described elsewhere herein, when electrons of sufficient energy strike scintillator 20 of Scintillator-SiPM coupled pair assembly 24, light photons 30 are emitted and some are incident upon SiPM 21 of the Scintillator-SiPM coupled pair assembly 24. The resulting output current is proportional to the light intensity emitted by scintillator 20, which in turn is proportional to the instantaneous electron intensity striking the front face 26 of the scintillator 20. In the exemplary embodiment, the output current of SiPM 21 is provided to a Transimpedance amplifier (TIA) which can be mounted on the same PCB 23, mounted on a connected but separate PCB which is placed in close proximity to the Scintillator-SiPM coupled pair assembly 24, or mounted directly on the vacuum side of the feed-through 36, such TIA converting the SiPM current to a voltage pulse. In all of the aforementioned implementations, the TIA placement inside the sample chamber 3 or column 2 benefits from a much lower noise environment than if it were placed outside the sample chamber 3 or column 2, where it can be exposed to a multitude of noise-generating equipment and power supplies. In the preferred configuration, the output of the TIA is connected to the in-vacuum side of a multi-pin vacuum feed-through. Placement of the TIA can indeed be outside the sample chamber 3 or column 2 when placement inside the sample chamber 3 or column 2 is restricted. Wires 37 then provide the input to control system 16, wherein the signal is digitized or otherwise directly used to modulate the brightness of a monitor in display system 17. The signal from the Scintillator-SiPM coupled pair assembly 24 is measured in synchronism with the pixel by pixel raster scan of the beam 7 of primary electrons; in this way an image of the scanned region of the sample 13 is formed. The resulting image magnification is the ratio of a linear dimension in the acquired image to the corresponding dimension on the sample scanned by the incident electron beam 7. Thus, according to one aspect of the present invention, Scintillator-SiPM coupled pair assembly 24 is used to measure instantaneous electron intensity of backscattered electrons (BSE) generated in SEM 1.

As stated elsewhere herein, several key benefits provided by SiPM 21 include high gain, small form factor, and low operating voltage (35V compared to 1 kV typical in a PMT). The small form factor of the PCB-mounted scintillator-SiPM coupled pair assembly 24 is of particular importance to the present invention as it allows a plurality of assemblies to be positioned in strategic positions inside the column 2 or sample chamber 3 of SEM 1, without requiring the use of a chamber access port. This has a two-fold effect: 1) it allows for multiple imaging vantage points of samples in the SEM 1, which may improve the information content provided by the SEM 1, and 2) it frees up ports for use with other types of detectors or manipulators, which, in the prior art, would have been occupied by PMTs. Also, as stated above, this allows the electron detector 18 to be positioned in the region in between sample 13 and the pole piece of objective lens 12 while maintaining a short working distance 11. The Scintillator-SiPM coupled pair assembly 24 also eliminates the need for a light guide and its associated expense. Moreover, as described elsewhere herein, the back face 27 of the scintillator 20 is directly connected face-to-face with the light sensing surface 29 of the SiPM 21 by a thin film of light-transmitting adhesive agent 22, rather than being limited to connection through the edges of the scintillator disc as in prior art, and increased light collection efficiency is achieved. In the prior art, the amount of light collected by the light guide through the edges of a 15 mm diameter, 1 mm thick scintillator averages only 5-7% of the light generated in the disc for simple designs, while careful optimization of the design and coupling can improve the efficiency to perhaps an average of 15%. If light could be removed from the entire back surface of the same disc, however, the efficiency would improve to 60%. In the case of the scintillator-SiPM coupled pair assemblies 24, the entire back is always used for collection. Therefore, for a given area, the Scintillator-SiPM coupled pair assembly 24 can be more efficient by a factor 4 when positioned optimally under the pole piece of the final lens.

While in the exemplary embodiment described above, electron detector 18 has been optimized to monitor backscattered electrons, it will be understood that electron detector 18 may also be optimized to monitor secondary electrons. Often, an SEM contains two or more electron detectors, each optimized in a certain way. Because of the energy difference between secondary and backscattered electrons, different detector configurations may be required for the two signals, and the final images contain different information content. As noted elsewhere herein, an SED requires bias voltages to draw the SEs from the sample surface toward the detector and to accelerate them to sufficient energy to activate the scintillator, but in serving this function, the bias voltage can also bend low energy electrons around topographic features from regions of the sample that do not have line of sight to the detector. The backscattered electrons are of much higher energy, up to the energy of the primary beam 7, eliminating the need for the bias voltage, and retaining the shadowing information to more reliably produce an image representing the topography of the sample.

As seen in FIG. 1, SEM 1 also includes an X-ray detector 38. The intensity of a BSE signal is strongly related to the atomic number (Z) of the sample 13. Thus, in one embodiment, the BSE signal collected by electron detector 18 configured to collect backscattered electrons is used to supplement the X-ray detector 38 which provides direct elemental analysis.

Figure 8:
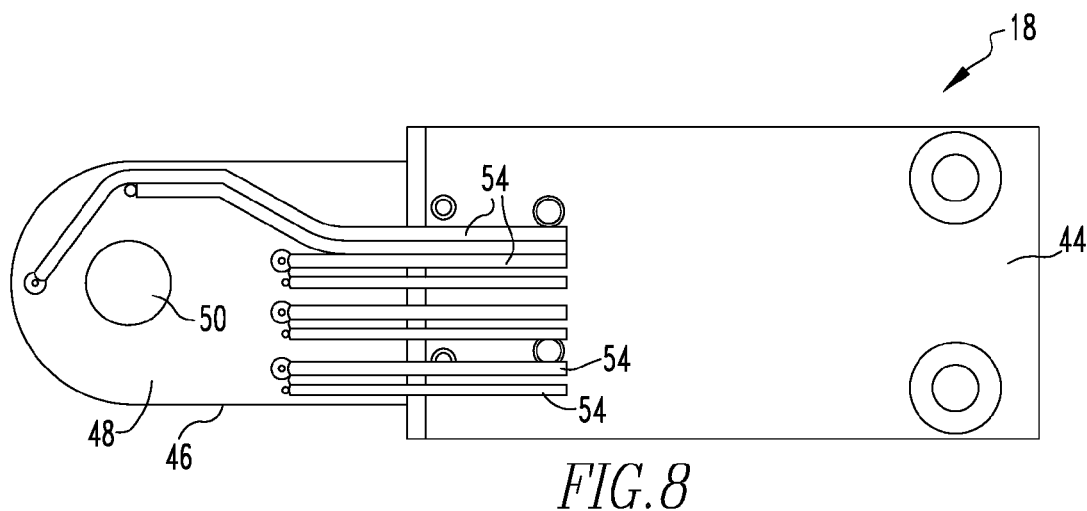
FIGS. 8, 9 and 10 are top plan, bottom isometric and enlarged views, respectively, of one particular embodiment of an electron detector that may be employed in the SEM of FIG. 1 as an annular backscattered electron detector, mounted directly under the pole piece, with the center of the annulus being positioned on the centerline of the electron column.
Figure 9:
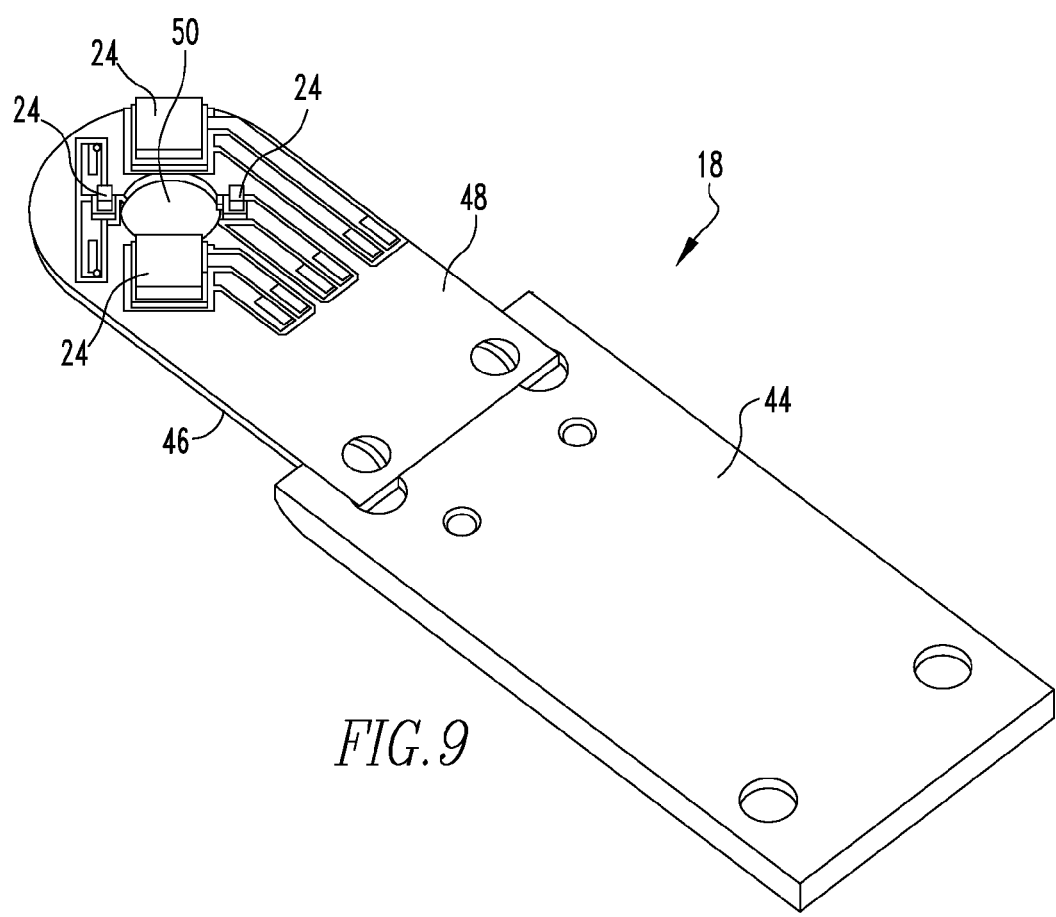
Figure 10:
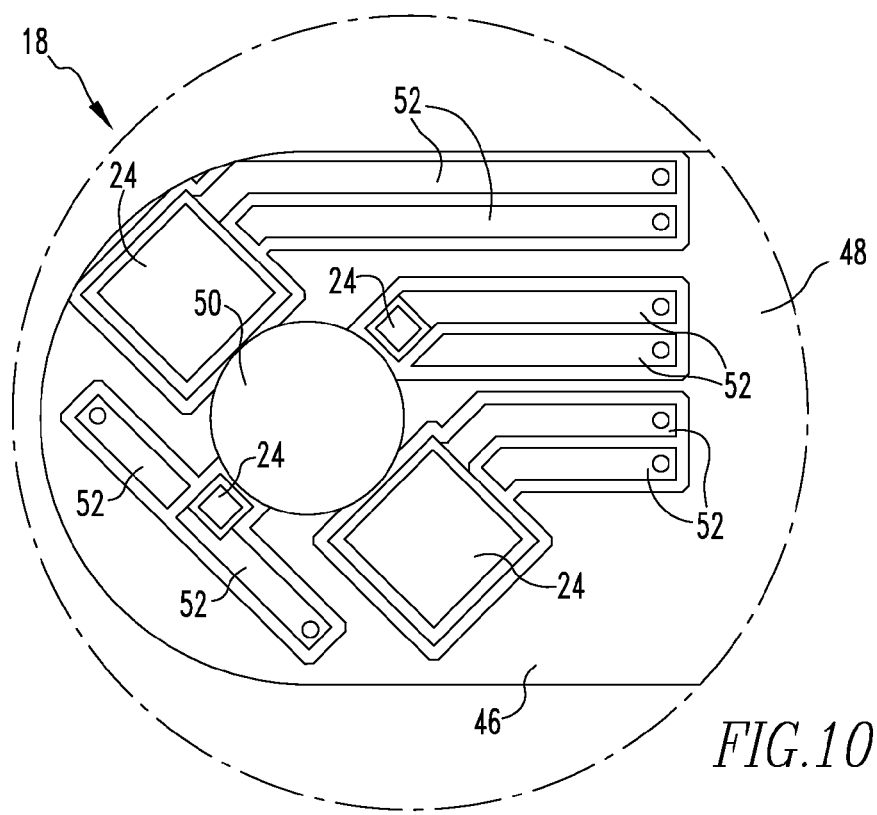

BSEDs are typically annular devices placed directly under and as close as possible to the pole piece of the objective lens of an SEM. This configuration allows the sample to be placed at a short working distance, thereby providing high image resolution and high BSE intensity while still retaining a near 90° line-of-sight from the sample to the detector. FIGS. 8, 9 and 10 are top plan, bottom isometric and enlarged views, respectively, of one particular embodiment of electron detector 18 that may be employed in SEM 1 as a BSED.

In this embodiment, electron detector 18 includes a mounting bracket 44 that is used to mount electron detector 18 within sample chamber 3 (or, alternatively, column 2). A PCB assembly 46 is attached to the distal end of mounting bracket 44. PCB assembly 46 includes a substrate 48 having a pass-through 50 that is structured to allow electron beam 7 to pass through electron detector 18 so that it can reach sample 13. In the illustrated embodiment, pass-through 50 is circular such that the distal end of PCB assembly 46 has a generally annular shape, but can also be square or rectangular. In one particular exemplary embodiment, PCB assembly 46 is structured to prevent charging from incident backscattered or secondary electrons and to carry the required grounding and bias voltage(s).

As seen in FIGS. 8 and 9, this embodiment of electron detector 18 includes four independent Scintillator-SiPM coupled pair assemblies 24 (with YAG:Ce scintillators in the exemplary, non-limiting implementation), as described elsewhere herein, that are provided on the bottom of substrate 48. In particular, two 1 mm$^2$ Scintillator-SiPM coupled pair assemblies 24 are provided opposite each other on one axis, and, on an axis 90° to the first, two 16 mm$^2$ (4 mm×4 mm) Scintillator-SiPM coupled pair assemblies 24 are provided opposite each other. It will be understood, however, that the concept extends to a variable number of discrete devices and a range of sizes up to approximately 1 cm$^2$ in one embodiment. In addition, such symmetrical spacing, when used in combination with normal electron beam incidence on the sample 13, provides balanced topographical views.

Conductive traces 52 are provided on the bottom surface of substrate 48 for making electrical connections to the Scintillator-SiPM coupled pair assemblies 24. Also, as seen in FIG. 8, wires 54, which allow for electrical connections from control system 16 to be made to electron detector 18, run on the top surface of substrate 48. Wires 54 extend through holes provided in substrate 48 and are soldered to conductive traces 52. In the exemplary embodiment, each Scintillator-SiPM coupled pair assembly 24 or sets of Scintillator-SiPM coupled pair assemblies 24 can be turned on or off independently. In addition, their outputs can be manipulated by appropriate electronic circuitry or software, wherein, for example, all the outputs can be summed together to create an image with strong compositional contrast, or the signals from the devices on one side of the centerline of column 2 can be used to create an image with strong topographical contrast. This capability thus mimics a segmented detector using photodiodes, but provides the gain and speed of a scintillator detector.

This design (involving the use of different size scintillator-SiPM coupled pair assemblies 24) was chosen to learn the tradeoffs between the device size and the active area of collection.

Figure 11:
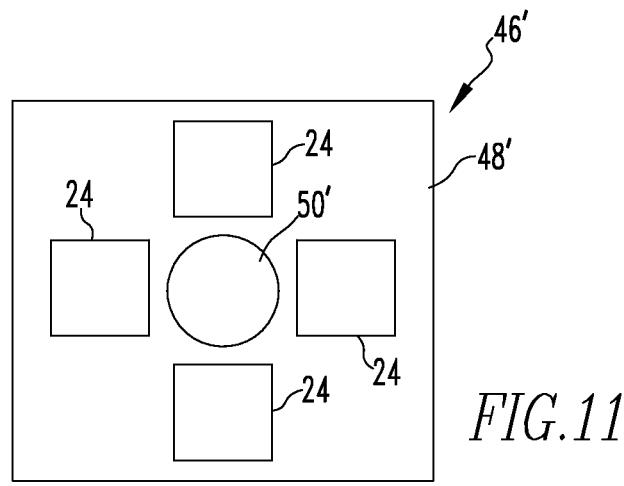
FIGS. 11, 12 and 13 are schematic diagrams of various alternative PCB assemblies that may be used to form an electron detector that may be employed in the SEM of FIG. 1.
Figure 12:
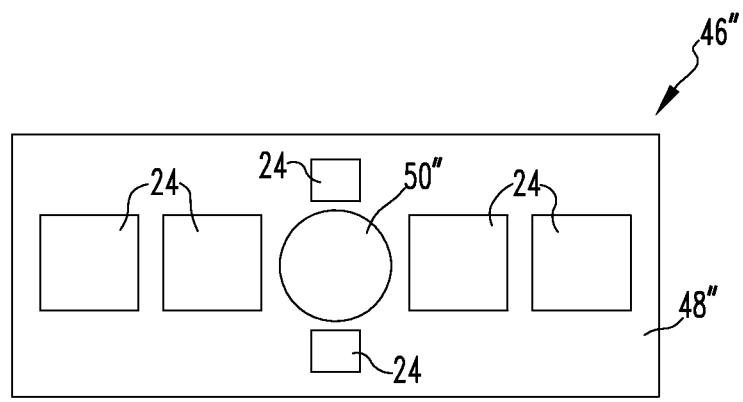
Figure 13:
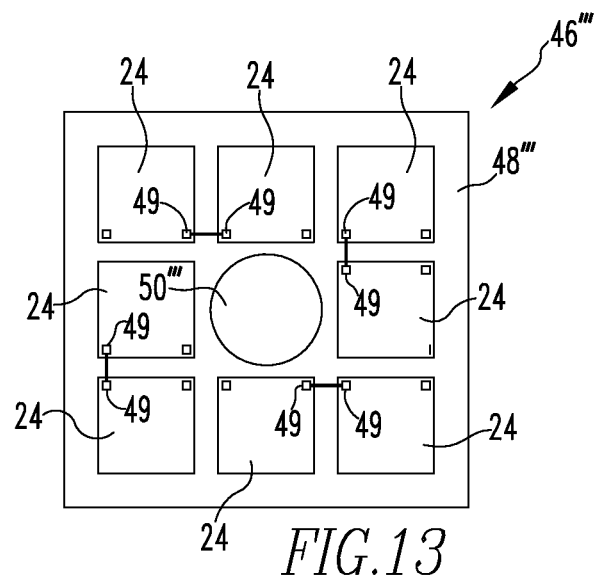

FIGS. 11-13 show other possible PCB assembly configurations that may be employed in alternative electron detector embodiments (i.e., in place of PCB assembly 46). In particular, FIG. 11 shows a PCB assembly 46' that includes four 4 mm×4 mm (16 mm$^2$) scintillator-SiPM coupled pair assemblies 24 spaced evenly about pass-through 50' of substrate 48'. FIG. 12 shows a PCB assembly 46" that includes two adjacent 4 mm×4 mm (16 mm$^2$) scintillator-SiPM coupled pair assemblies 24 positioned on one side of pass-through 50" of substrate 48" with two more adjacent 4 mm×4 mm (16 mm$^2$) scintillator-SiPM coupled pair assemblies 24 positioned on the opposite side of pass-through 50" of substrate 48". In addition, two 1 mm×1 mm (1 mm$^2$) scintillator-SiPM coupled pair assemblies 24 are positioned on opposite sides of pass-through 50" in between the 4 mm×4 mm scintillator-SiPM coupled pair assemblies 24. FIG. 13 shows a PCB assembly 46''' that includes eight 4 mm×4 mm (16 mm$^2$) scintillator-SiPM coupled pair assemblies 24 spaced about pass-through 50''' of substrate 48'''. Note that in the embodiment of FIG. 13, the bonding pads 49 of the SiPM 21 are identified, and adjacent pairs of the 4 mm×4 mm scintillator-SiPM coupled pair assemblies 24 are connected together. The rationale for this will be described below.

The embodiments of electron detector 18 shown in FIGS. 8-13 enable control system 16, and the associated software, to acquire an image from each of the scintillator-SiPM coupled pair assemblies 24 independently or to sum any number or all of them together. In the prior art, the use of 2 or 4 photodiodes or bulk APDs placed symmetrically around the column centerline enabled the collection of an image from one side of the centerline only, to provide a topographical view of the specimen, or, alternatively, the collection of the image from all of the segments to provide an image dominated by composition contrast. In the prior art, the use of scintillator discs, which provided faster and brighter images, do not allow this segmentation without the use of multiple scintillators, light pipes and PMTs, which is impractical in many situations, due to the space consumed by the multiple detectors as well and the added cost. The devices proposed herein enable segmented image capability, while providing the speed and intensity per unit area of the scintillator disc of the prior art.

Figure 14:
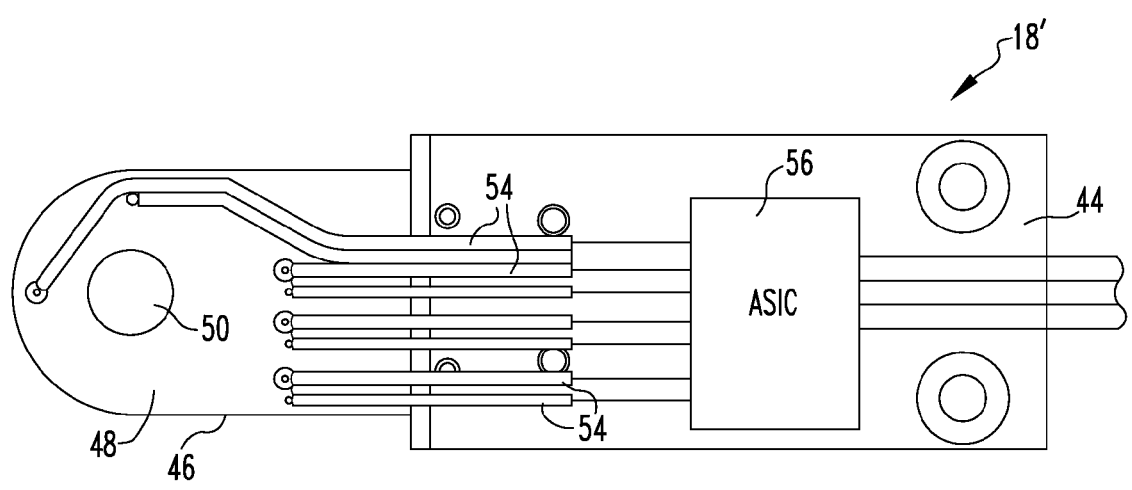
FIG. 14 is a top plan view of another particular embodiment of an electron detector that may be employed in the SEM of FIG. 1 as a backscattered electron detector.

With respect to segmentation, there is not expected to be much advantage in increasing the number of segments, while the complexity of the electronics increases in proportion to the number of channels. Therefore, in FIG. 13, we choose to use two devices per channel, increasing the active area while not increasing the complexity of the electronics. This is a unique implementation. In conventional systems, semiconductor detectors (direct electron detectors) are used because of simplicity of mounting them in a similar configuration to that shown in FIG. 10 in order to obtain the segmentation and the ability to choose compositional or topographical imaging. Electron detector 18 is able to take advantage of the higher gain of the SiPM 21 over direct electron detectors ($10^6$ compared to $10^2$-$10^3$ for standard photodiodes), yet retain the small size and mounting simplicity. In addition, the use of the Scintillator-Scintillator-SiPM coupled pair coupled pair assemblies 24 as compared to four standard photodiodes enables imaging at much faster scanning rates (up to 100 nS per pixel for present devices) based on the design of the SiPM and its use in Geiger mode compared to bulk devices. Another advantage of the small size of the Scintillator-SiPM coupled pair Scintillator-SiPM coupled pair assemblies 24 is the possibility to use ASIC electronics mounted on mounting bracket 44 or substrate 48, in close proximity to the Scintillator-SiPM coupled pair assembly 24, i.e., the signal source. This is demonstrated in FIG. 14, wherein ASIC chip 56 is mounted on mounting bracket 44 in further alternative electronic detector 18'. In the exemplary embodiment, ASIC chip 56 implements TIA amplifier functionality wherein it is coupled to each SiPM, receives the signal of each SiPM, converts the current pulse generated in each SiPM to a voltage pulse, and then amplifies each voltage pulse. This close coupling of the Scintillator-SiPM coupled pair assembly 24 and the signal processing electronics of ASIC chip 56 has the potential of minimizing noise that could be picked up over the signal wire(s) leading outside the sample chamber 4 to remote electronics. Although we describe ways to mount the TIA functionality close to the signal source, the largest benefit is most likely to accrue simply from keeping the TIA inside the sample chamber 3 or column 2, to shield the wires carrying the signal from the SiPM 21 and the TIA itself from the many noise sources existing outside the sample chamber 3 or column 2, mounting it directly to the vacuum side of the feed-through 36, perhaps with flexible cable to the SiPM 21, such that minimum size and maximum mobility of the electron detector described herein can be maintained.

Figure 15:
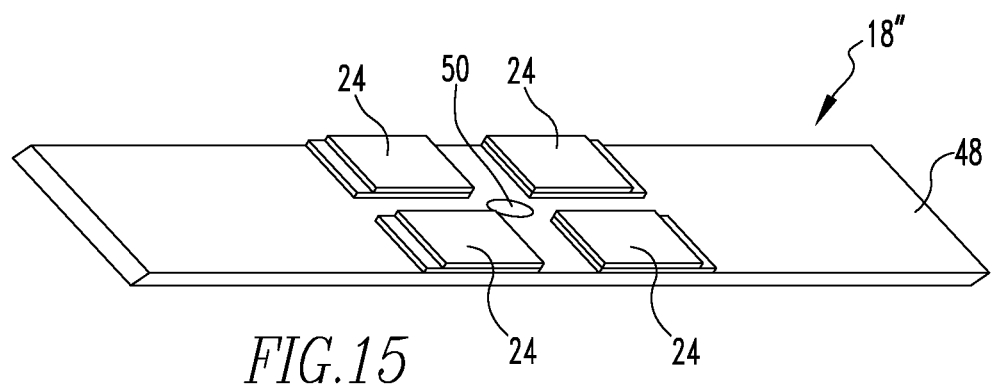
FIG. 15 is a schematic diagram of a small size electron detector according to another exemplary embodiment.

An example of a small size electron detector 18" according to another exemplary embodiment is shown in FIG. 15. This device illustrates four 1 mm×1 mm scintillator-SiPM coupled pair assemblies 24 mounted on a PCB substrate 48 that is 3.5 mm wide by 10 mm long and a total thickness, including PCB substrate 48, less than 2 mm. The device shown in FIG. 15, of course, is not the smallest device that can be conceived, as the PCB 48 can be reduced in width by using only two scintillator-SiPM coupled pair assemblies 24 and significantly in length by optimized bonding methodologies.

Figure 16:
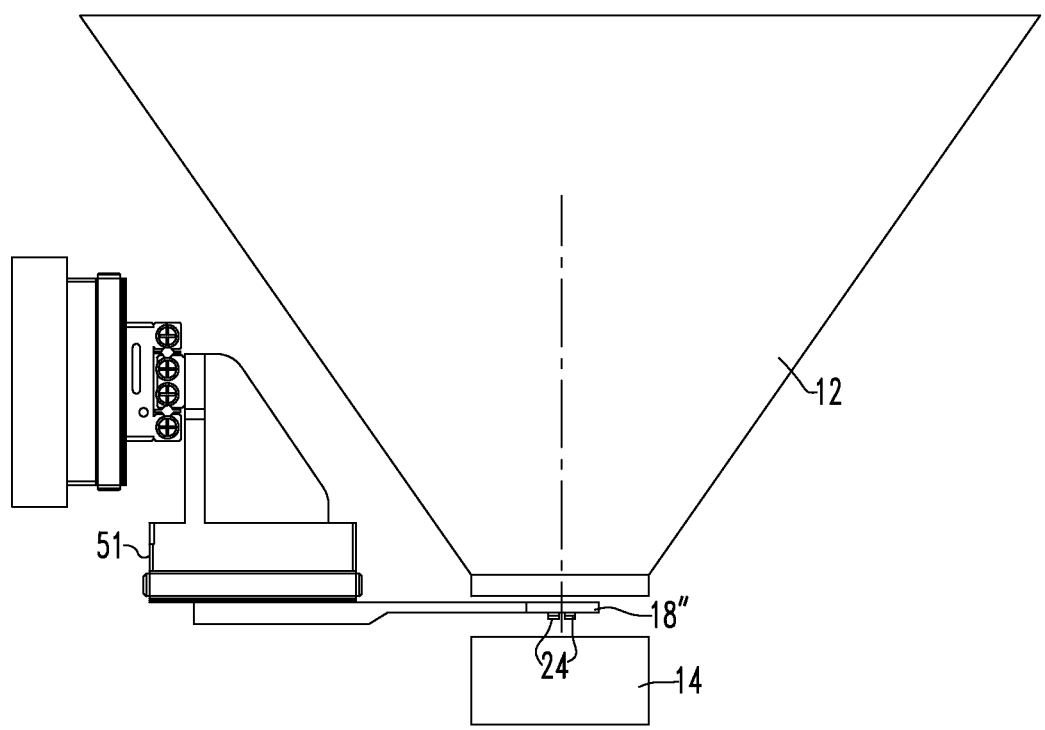
FIGS. 16 and 17 are schematic diagram of the small electron detector of FIG. 15 (employing only two scintillator-SiPM coupled pair assemblies) is mounted on the end of a mechanical positioning device in an SEM.
Figure 17:
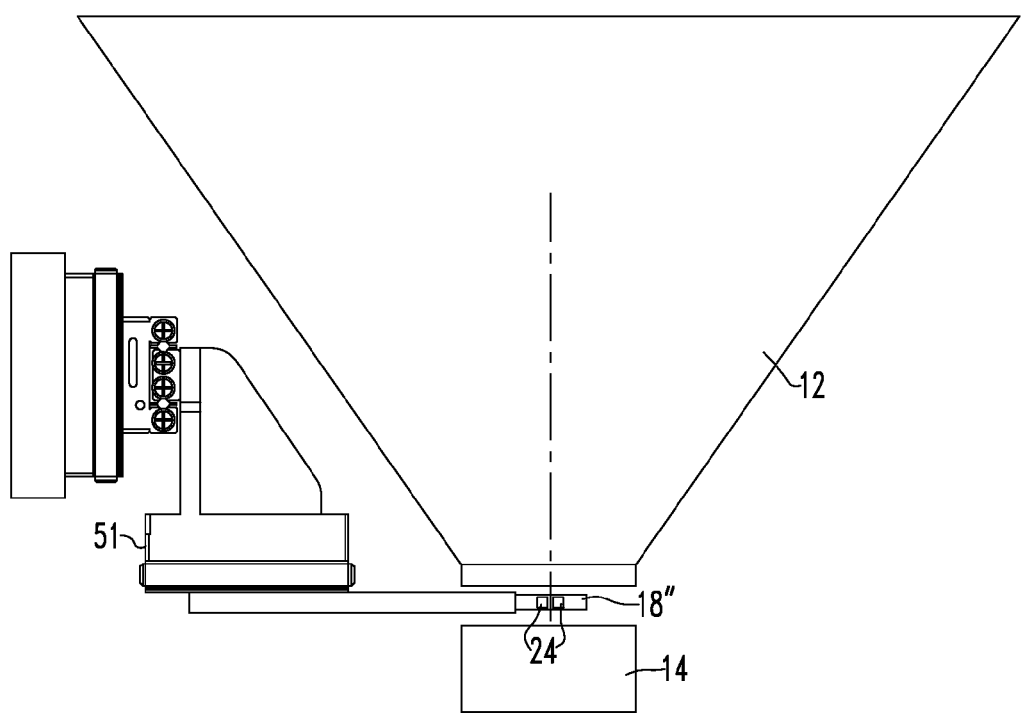

Another exemplary embodiment which both relies on and takes advantage of the small size and high mobility of the electron detector embodiments described herein is shown in FIGS. 16 and 17, in which the small electron detector 18" of FIG. 15 (employing only two scintillator-SiPM coupled pair assemblies 24) is mounted on the end of a mechanical positioning device 51. In this manner, the electron detector 18" can be brought to the sample, and indeed to specific regions of the sample. It can be positioned such that the hole 50 is used as a pass-through for the electron beam (FIG. 16), or it can be positioned such that the two scintillator-SiPM coupled pair assemblies 24 face the sample from the side (FIG. 17). In the latter mode, the sample can be tilted at a high angle (shallow beam incidence) and the electron detector 18" in FIG. 17 becomes a Forward Scattered Electron Detector (FSED). The FSEs, and therefore their resulting images, are influenced significantly by crystal orientation and diffraction. Such orientation contrast is not visible in the normal BSE or SE images because the detectors are rigidly fixed in a position that is unable to achieve the forward scattered geometry.

Furthermore, backscattered electron detectors in an SEM must typically operate over a wide dynamic range because the primary electron beam current can vary from a few picoamps to more than 100 nanoamps depending on the intent of the user and type of sample. For a given average atomic number, primary beam conditions, and geometric arrangement, the BSE intensity will scale according to the primary beam current. In the present invention, SiPM 21 is able to handle the required dynamic range by means of a high pixel density and appropriate adjustment of the bias voltage. However, at very low beam currents, which are used to obtain best image resolution or because the sample is extremely beam sensitive, the inherent thermal noise in SiPM 21 can be minimized for best performance by lowering its operating temperature. It is known that thermal noise in Silicon decreases by 50% with every 10° C. reduction in operating temperature.

Figure 18:
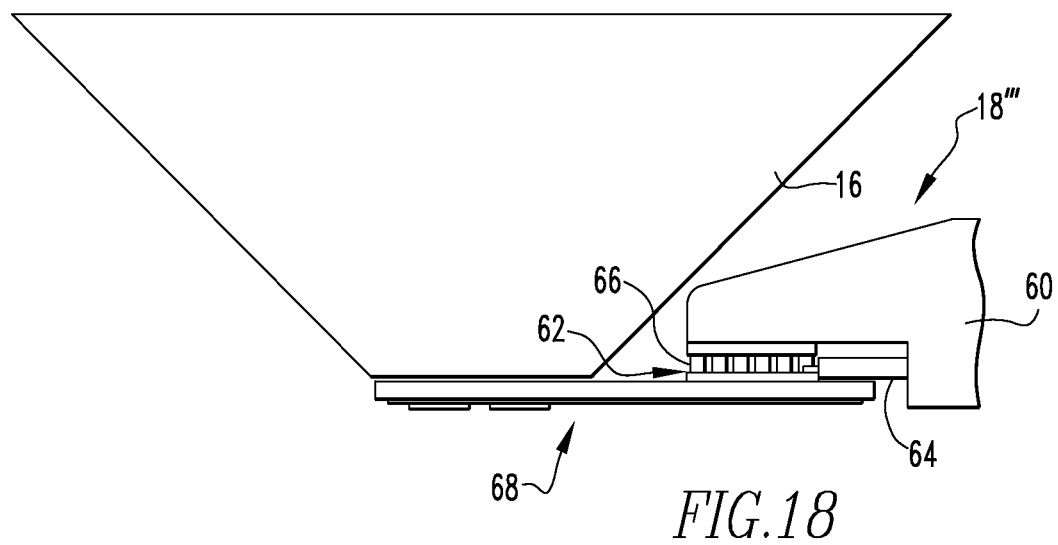
FIGS. 18 and 19 are front elevational and isometric views, respectively, of an electronic detector according to another alternative embodiment that may be employed in the SEM of FIG. 1 as a backscattered electron detector that is structured for optimum performance by cooling the SiPM thereof.
Figure 19:
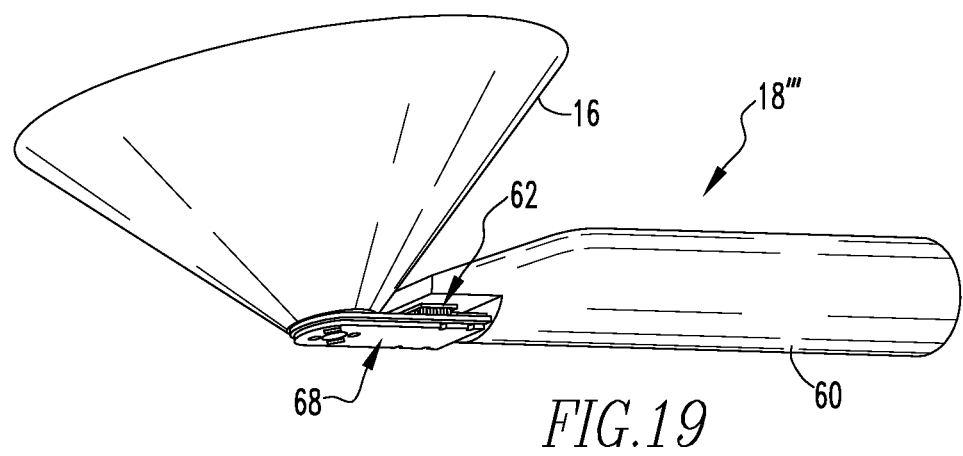

FIGS. 18 and 19 are front elevational and isometric views, respectively, of an electronic detector 18'" according to another alternative embodiment that may be employed in the SEM of FIG. 1 as a BSED that is structured for optimum performance by cooling SiPM 21. In FIGS. 18 and 19, electronic detector 18''' is shown mounted inside sample chamber 3 of SEM 1 at a position below the pole piece of objective lens 12 of SEM 1. In this embodiment, electron detector 18''' includes a mounting arm 60 that is used to mount electron detector 18''' within sample chamber 3. In addition, a cooling assembly 62 is coupled the distal end of mounting arm 60. In the illustrated embodiment, cooling assembly 62 includes a Thermoelectric Cooler (TEC) 66 (which, as is known, employs the Peltier effect) that is coupled to a heat pipe 64 (or simply a copper rod or cold finger). A PCB assembly 68 is coupled to TEC 66.

Figure 20:
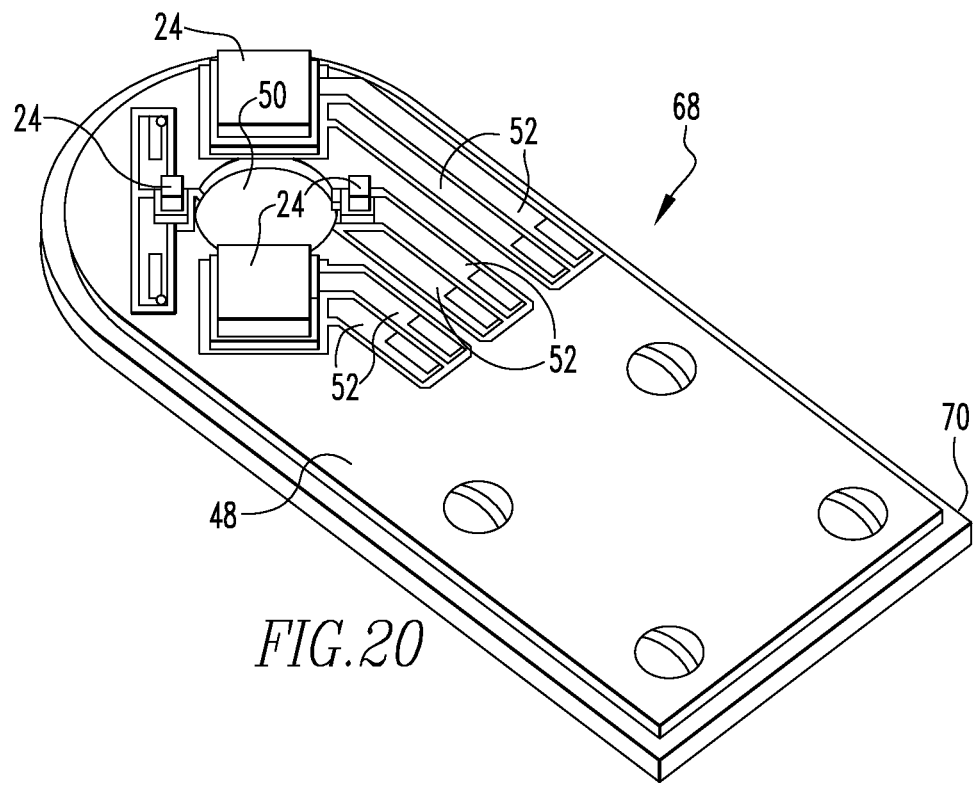
FIG. 20 is an isometric view of a PCB assembly of the electronic detector of FIGS. 18 and 19.

FIG. 20 is an isometric view of PCB assembly 68. PCB assembly 68 includes a number of the same components as PCB assembly 46 (FIGS. 8-10), including substrate 48 having pass-through 50, Scintillator-SiPM coupled pair assemblies 24, and conductive traces 52 (electrical connections to conductive traces 52 may be in the form of a flex circuit or a wire bundle). In addition, substrate 48 is provided on thermal conductor member 70, which in the illustrated embodiment is a metal (e.g., copper) spreader. As seen in FIG. 18, thermal conductor member 70 is coupled to heat pipe 64 through TEC 66.

In operation, TEC 66 cools thermal conductor member 70, which in turn cools substrate 48 and Scintillator-SiPM coupled pair assemblies 24 (temperature distribution is kept even across SiPM 21). Heat is removed to an external heat sink (not shown) by means of heat pipe 64. In one particular, non-limiting embodiment, heat pipe 64 delivers heat outside sample chamber 3 via vacuum feed-through 36 provided in sample chamber 3. In an alternative embodiment, TEC 66 may be placed outside sample chamber 3, with heat pipe 64 providing the thermal connection between thermal conductor member 70 and TEC 66.

In the exemplary embodiment, the temperature reduction target of the cooling assembly 62 is at least 50° C. (i.e., $\Delta T \approx 50°$ C.), which would suggest an achievable operating temperature in the range of $-20°$ C. and a reduction of the intrinsic thermal noise (dark current) of the SiPM 21 by a factor of 16. A larger $\Delta T$ can be achieved by appropriate selection of the particular TEC 66 and thermal design, to achieve a lower operating temperature, but then condensation may become a factor when sample chamber 3 is vented for sample exchange. It is envisioned that if an operating temperature less than $-20°$ C. is desirable or required, an interlock to the vent control on SEM 1 can insure that the device warms up sufficiently before air is introduced into sample chamber 3 (using either a time delay or a heating element).

Recently, it is becoming more and more common in high resolution instruments to use detectors which are positioned inside the electron column of an SEM and which detect electrons that originate at the specimen surface and follow the path close to the optical axis of the column, i.e. they go back inside of the column. Those electrons re-enter through the final focusing lens of the SEM column (the objective lens) and are detected somewhere inside of the objective lens or above it in the column. These devices are therefore called in-lens or through-the-lens detectors.

Typically, the advantage of using in-lens detectors is better electron collection efficiency and a higher imaging resolution, the latter obtained because the use of in-lens detectors enables the sample to be placed at extremely short working distance. Such detectors are therefore becoming common for SEMs, and are routinely provided in high-end, high resolution instruments. However, the major difficulty when implementing such in-lens detectors based on the standard scintillator-light guide-PMT setup described elsewhere herein is the size of the PMT (on the order of several centimeters in all directions). As a result, as also described elsewhere herein, in prior art applications the PMT must be positioned outside of the lens or column. In contrast, the scintillator must be positioned inside the column rather close to the column axis (e.g., around the axis for an annular type detector). In addition, the PMT and scintillator must be connected by a light guide.

The above described prior art configuration requirements bring a number of disadvantages. For example, as described elsewhere herein, the envelope of the column must incorporate bores/holes for getting the light guide to the outside PMT. If the detector is in the objective lens, the holes must go through the objective magnetic circuit that unavoidably disturbs the uniformity and symmetry of the magnetic field. The consequences of the non-uniform magnetic field are a higher saturation of the magnetic material in certain volumes (close to the holes) and aberrations in the final lens which degrade the ultimate image resolution achievable. In order to minimize this effect, whenever a bore is drilled in the column, a matching bore is drilled opposite to it, to balance any asymmetrical field changes that may be caused by the initial hole. In addition, there is a loss of light when it is transferred through the light guide. The light guide also occupies space inside the column as well as in the chamber where it extends from the objective lens to the chamber wall. Furthermore, the light guide cannot be positioned freely along the column axis as it has to go out of the column and it could interfere with other parts (for example with the lens coil). Therefore the position of the detector in the prior art is limited to certain space and such position may not be optimal for maximum detection efficiency.

On the other hand, as noted elsewhere herein, SiPMs, such as SiPM 21, are very small devices, and a given Scintillator-SiPM coupled pair assembly 24, mounted and bonded onto a PCB, can be as thin as 1.5 mm or even less. Thus, in one aspect of the present invention, an in-lens or through-the-lens detector is implemented by placing a Scintillator-SiPM coupled pair assembly 24 completely inside of the column or objective lens. In such a case, the device and its mounting would not disturb the column envelope or magnetic circuit by the requirement for bores and holes (only wires are needed to connect with the external electronics). Also, as noted elsewhere herein, direct coupling of scintillator 20 to SiPM 21 would minimize light losses, since no light guide is required. There is also the possibility of direct detection of the electrons (without a scintillator), which would make the device even smaller.

Figure 21:
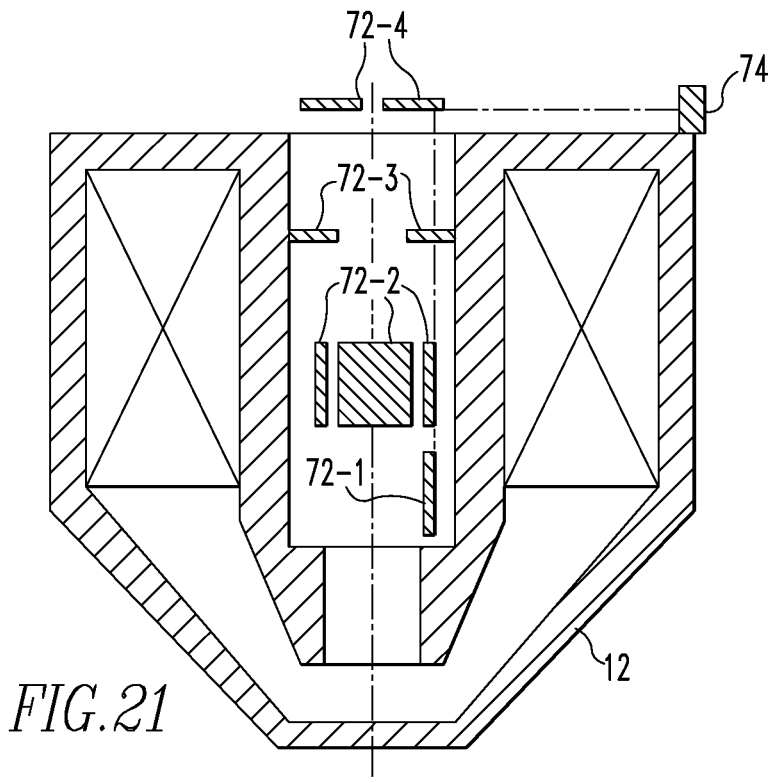
FIG. 21 shows a number of possible positions and configurations of SiPM-based detectors inside the column or objective lens of the SEM of FIG. 1.

FIG. 21 shows a number of possible positions and configurations of SiPM-based detectors 72, each including an Scintillator-SiPM coupled pair assembly 24 as described herein, according to alternative embodiments of the invention. In all cases, the SiPM-based detectors 72 is inside the electron column 2 and/or objective lens 12 and requires no drilling through the lens magnetic circuit as the signal is led out using wiring and feed-through 74, which can be positioned outside of objective lens 12. A detector 72 placed with its active surface parallel to the column axis can be a one segment (72-1) or multi-segment (72-2) configuration, enabling azimuthally resolved collection of the electrons. An annular type detector 72 can be positioned inside (72-3) or above (72-4) objective lens 16. Such annular type detector 72 may have different ID and OD diameters or may be radially segmented in order to collect different portions of angularly distributed electrons. Due to the very small size of such detectors 72, it may be possible to place several detectors 72 in one objective lens 16 and collect multiple signals, therefore getting multiple information about the electron distribution (e.g. for angularly or axially resolved detection). It may be possible to place several detectors 72 in multiple locations within column 2 or sample chamber 3 for unique imaging perspectives, low magnification views, and macro-imaging of the sample 13 using montage imaging techniques.

Figure 22A:
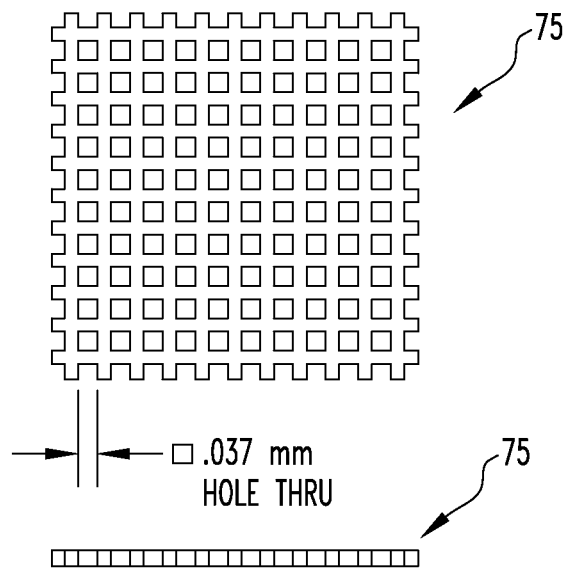
FIGS. 22A and 22B are schematic diagrams showing a typical 400 mesh EM Nickel grid from different angles.
Figure 22B:
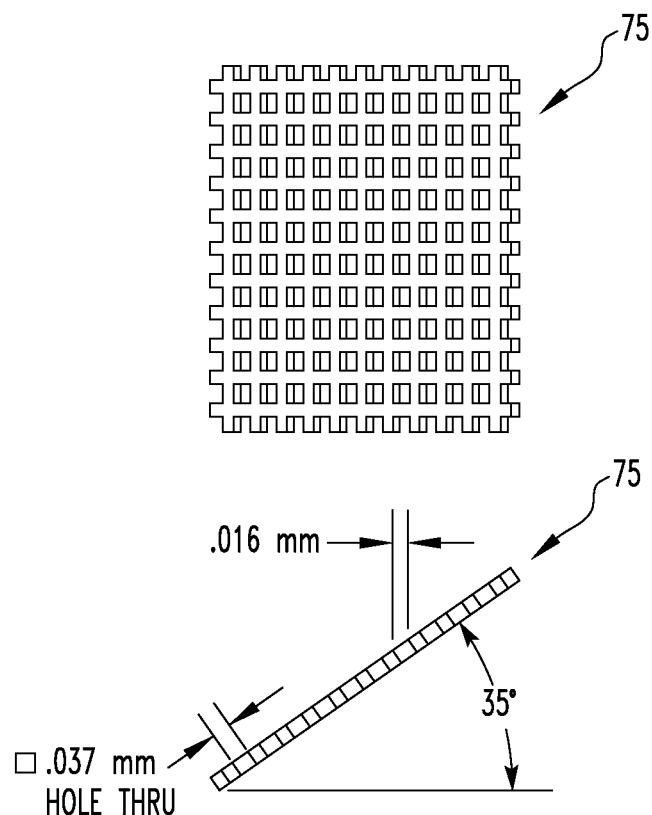

The BSED is usually mounted under the pole piece of the final lens, as described earlier, while an Energy Dispersive X-ray (EDX) detector faces the sample from the side, at an angle typically of 35-45 degrees relative to the sample surface, such sample surface being horizontal when the typical normal electron beam incidence is used. The most common type of EDX detector currently used is called an SDD (Silicon Drift Detector), but Lithium-drifted Silicon detectors are used as well. Both the EDX detector and the BSED are line-of-sight detectors, and therefore, each will have different views of the sample. X-rays may be shadowed by surface topography while the BSE detector, looking at the sample from a above, may have an unobstructed view. When attempts are made using prior art devices to match or correlate the two images, discrepancies will often occur which could cause misinterpretation or confusion of the feature-chemistry relationship. This effect is illustrated in FIGS. 22A and 22B, in which the left drawing shows a typical 400 mesh EM Nickel grid 75 in a plan view from the top, while the right drawing shows the view from the same position when the grid 75 is tilted 35 degrees (tilt angles shown below in the FIGS,). An elemental image of Ni provided by the EDX detector would have a compressed view, such as the grid 75 in FIG. 22B, while the backscattered detector will have the correct view shown in FIG. 22A.

The poor correlation between the BSE image and the X-ray image based on line-of-sight differences is addressed in yet another embodiment of the present invention, wherein a Scintillator-SiPM coupled pair based electron detector may be integrated on or close to the same axis as the EDX detector 38 in FIG. 1. FIGS. 23A and 23B show one implementation of such a combined EDX-BSED system, labeled with reference numeral 75, in which an electron detector 18", similar to the one shown in FIG. 15 but with only two scintillator-SiPM coupled pair assemblies 24, is mounted on the top external surface 76 of electron trap housing 77 of system 75. System 75 also includes an X-ray sensor 78, which in the illustrated, non-limiting embodiment is a silicon drift detector (SDD) and an electron deflection device 79 (e.g., a typical magnetic deflector often called an electron trap) positioned at an input end of electron trap housing 77. This type of deflector is necessarily included as an integral part of system 75 to prevent electrons from reaching X-ray sensor 78, which will create severe or even overwhelming background in the X-ray spectrum.

Figure 24A:
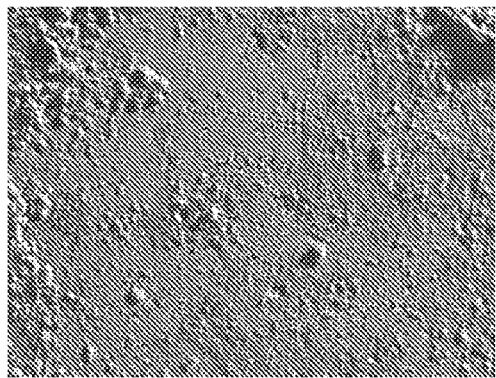
FIGS. 24A and 24B are two computer illustrated images, the image of FIG. 24A taken of a sample surface with an SEM having a Scintillator-SiPM coupled pair based electron detector mounted on the electron trap as shown in FIGS. 23A and 23B, and for comparison, the image of FIG. 24B taken with an annular photodiode detector (using the full area, in composition mode)
Figure 24B:
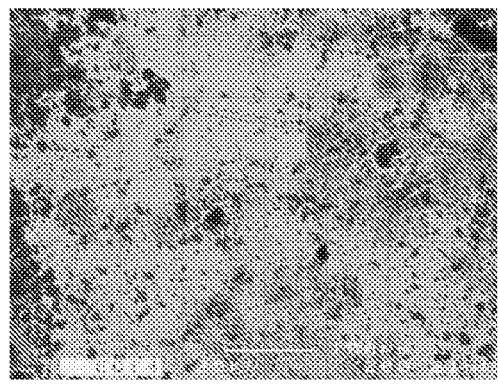

FIGS. 24A and 24B are two computer illustrated images, the image of FIG. 24A taken of a sample surface with an SEM having a Scintillator-SiPM coupled pair based electron detector mounted on the electron trap as shown in FIGS. 23A and 23B, and for comparison, the image of FIG. 24B taken with an annular photodiode detector (using the full area, in composition mode). The shadowing effects of the image of FIG. 24A are apparent, indicating that image was collected from the perspective of the upper right hand corner. The "set of tracks" in the upper center of the two images can be used for registration between the images.

Figure 24C:
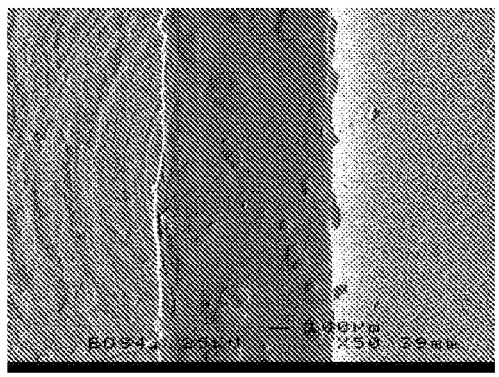
FIGS. 24C and 24D are two computer illustrated images that show the shielding effect that is encountered by line of sight detectors caused by topographical features in the line-of-sight.
Figure 24D:
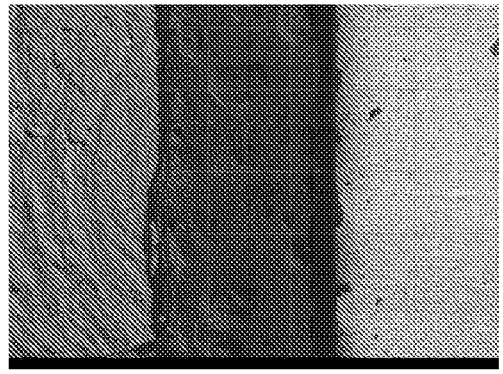

FIGS. 24C and 24D are two computer illustrated images that show the shielding effect that is encountered by line of sight detectors caused by topographical features in the line-of-sight. In this case, a strip of carbon tape is placed on the surface of an aluminum stub; in turn a strip of copper tape is placed on the column. The entire sample is then viewed from the side, at 35 degree elevation angle to the sample surface (which is horizontal). The pole piece mounted BSED image is 24C, and shows the true Al—C and C—Cu interfaces. The EDX detector, however, will see the effect of the shadows created by elevations of the tape, and will correlate more precisely with FIG. 24D, taken from the electron trap-mounted BSED described above.

Figure 25:
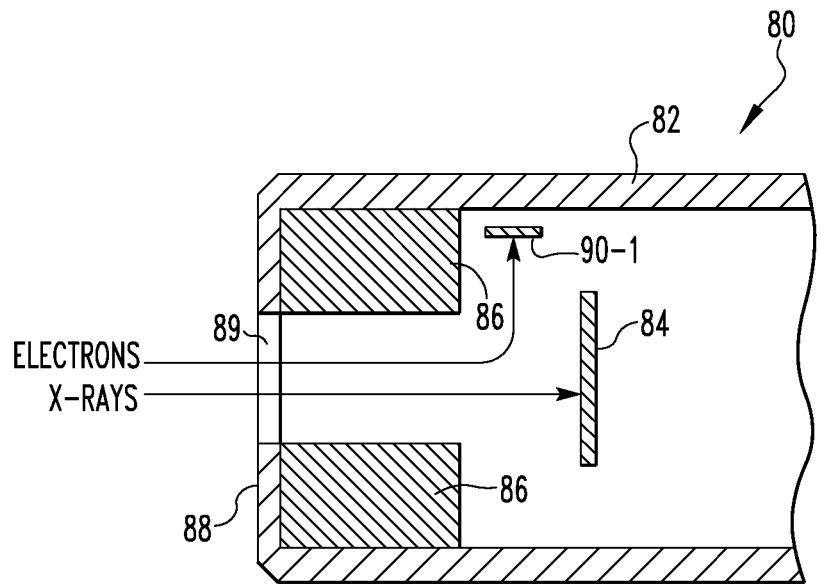
FIGS. 25-28 are schematic diagrams of various alternative embodiments of an X-ray detector of the SEM of FIG. 1 that includes an SiPM-based electron detector.

FIG. 25 is a schematic diagram of another exemplary implementation an X-ray detector 80 according to this embodiment (i.e., a combined EDX-BSED system). X-ray detector 80 includes a housing or "end cap" 82 that houses an X-ray sensor 84, which in the illustrated, non-limiting embodiment is a silicon drift detector (SDD) cooled by a TEC to typically negative 20° C. (although the operating range can be from about negative 10° to negative 65° C.). X-ray detector 80 also includes an electron deflection device 86 (e.g., a typical magnetic deflector often called an electron trap) positioned at an input end 88 of housing 82 adjacent to an opening 89 provided in input end 88. Electron deflection device 86 is configured such that the N pole of one segment thereof (positioned on one side of the longitudinal axis of the housing 82) faces the S pole of the other segment thereof (positioned on the other side of the longitudinal axis of the housing 82), the field being through the thickness of the magnets. This type of deflector is necessarily included as an integral part of X-ray detector 80 to prevent electrons from reaching X-ray sensor 84, which would create severe or even overwhelming background in the X-ray spectrum.

In addition, X-ray detector 80 also includes one or more SiPM-based detectors 90 (similar to SiPM-based detectors 72), each including a scintillator-SiPM coupled pair assembly 24 as described herein, that are provided within housing 82. FIG. 25 shows one possible position and configuration of such an SiPM-based detector 90 within housing 82. In the embodiment of FIG. 25, an SiPM-based detector 90-1 is positioned on one side of the longitudinal axis of the housing 82 adjacent to the end of the first segment of electron deflection device 86. In operation, electrons are deflected in a first direction away from the longitudinal axis of the housing 82 and into the Scintillator-SiPM coupled pair 24 of detector 90-1. The configuration of detector 90-1 also exploits the characteristic that the SiPM, unlike its PMT counterpart, is not affected by magnetic fields.

Figure 26:
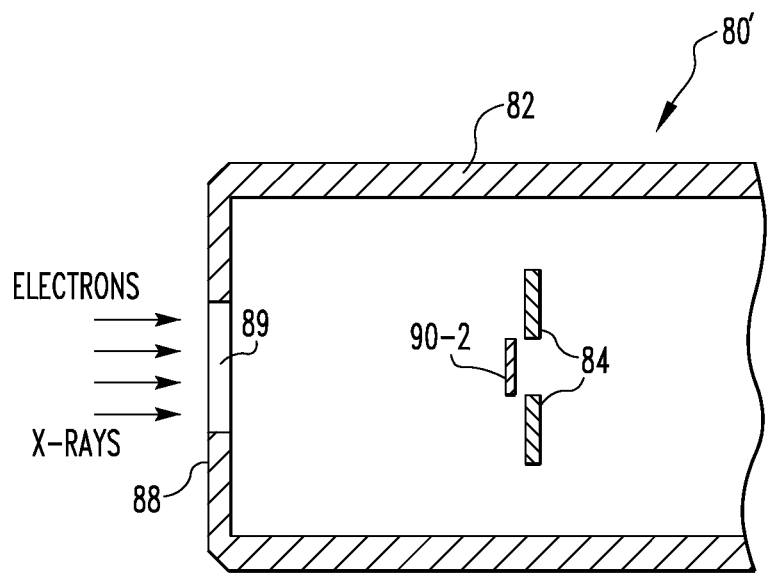
Figure 27:
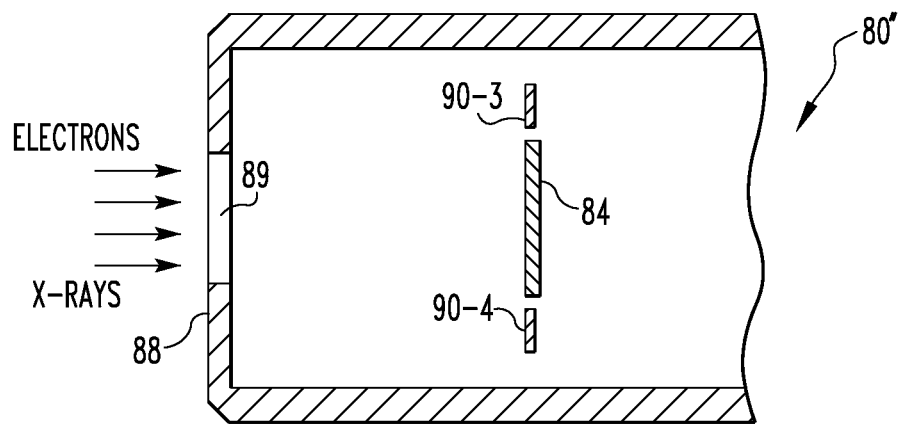

In another embodiment, shown in FIG. 26 as X-ray detector 80', an SiPM-based detector 90-2 may be mounted in or adjacent to the center of an annular X-ray sensor 84 (such as an annular SDD). In one particular embodiment, the SiPM-based detector 90-2 can be placed with its collection surface parallel with the surface of a SDD type X-ray sensor 84, wherein it could be mounted at the periphery of the SDD chip (FIG. 27). In this case, the magnetic deflection field is structured to be selectively and remotely turned on (active) and off (inactive) using mechanical, electrical or electromechanical means, such that the "off" position would allow the transmission of electrons to create a BSE image, and the "on" position would deflect them away (as in the normal operating mode for X-ray collection.

Figure 28:
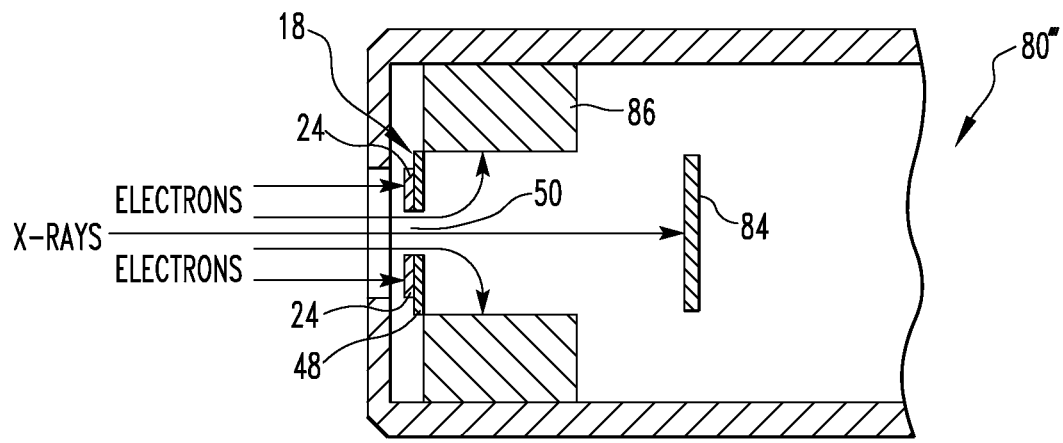

In still another alternative embodiment, shown in FIG. 27 as X-ray detector 80", one or more detectors 90 (e.g., detectors 90-3 and 90-4) can be placed around the periphery of annular or non-annular X-ray sensor 84, wherein the electrons are deflected away from X-ray sensor 84 and into the detectors 90-3 and 90-4 by suitable mechanism. In these embodiments, the cooling and heat dissipation used for X-ray sensor 84 can also serve to cool the detectors 90-2, 90-3 and 90-4. As a result, the dark current of the SiPMs 28 of the detectors 90-2, 90-3 and 90-4 may be reduced by reducing its operating temperature using the same cooling subassembly already incorporated in X-ray detector 80″ for cooling X-ray sensor 84. In yet another alternative embodiment, shown in FIG. 28 as X-ray detector 80‴, a detector 18 as described elsewhere herein is positioned along the longitudinal axis of the housing 82 in front of electron deflection device 86 in a manner such that pass-through 50 of detector 18 is aligned with opening 89. As a result, X-rays will be able to pass through detector 18 and reach X-ray sensor 84. In addition, number of electrons will be incident upon Scintillator-SiPM coupled pair assemblies 24 of detector 18 and will be detected thereby. Any electrons that are not incident upon Scintillator-SiPM coupled pair assembly 24 and that pass through pass-through 50 will be deflected by electron deflection device 86 and will not reach X-ray sensor 84. In all of the embodiments just described, the electrons focused or deflected into the detector(s) 90 can provide an image having the precise line of sight as the X-ray detector 38. In a further alternative of the embodiment of FIG. 28, a bias voltage may be applied to detector 18 (e.g., to the SiPMs 21 of the Scintillator-SiPM coupled pair assemblies 24) to attract attract/bend low energy electrons into detector 18 so that detector 18 will be able to detect more than just line of sight electrons.

FIG. 29 is a schematic diagram of an SEM 100 according to an alternative exemplary embodiment of the present invention that provides real time stereoscopy imaging. SEM 100 includes a number of the same components as SEM 1 described elsewhere herein (FIG. 1), and like components are labeled with like reference numerals. As seen in FIG. 29, SEM 100 also includes two scintillator-SiPM coupled pair detectors 102-1, 102-2 (similar to SiPM-based detectors 72), each including a Scintillator-SiPM coupled pair assembly 24 as described herein. Coupled pair detectors 102-1, 102-2 are provided within column 2 on opposite sides of electron beam 8. In the exemplary embodiment, coupled pair detectors 102-1, 102-2 are positioned above the sample in the sample chamber 3 or column 2 using any of the mounting modes described herein. In each case, the signal may be led out of column 2 from the coupled pair detectors 102-1, 102-2 using wiring and a feed-through as described elsewhere herein. The coupled pair detectors 102-1, 102-2 are used to generate two angularly offset image signals from backscattered Those image signals are streamed at TV rates and displayed alternately on monitor 40 in the fashion of 3D TV. Using active shutter glasses 104 (also known as liquid crystal shutter glasses), a real time image with 3D characteristics can be seen by the operator as specimen 22 is traversed.

SiPMs, although sensitive to electrons, have traditionally been optimized for the detection of photons emitted by a scintillator, such as scintillator 26. This is the case because traditionally, the surface layers of SiPMs have been optimized for transmission of light having wavelengths in the range of 450 to 600 nm. These layers, optimum for light transmission, absorb electrons and do not allow them to impinge on the active surface of the SiPM. According to a further embodiment of the invention, the process technology can be altered to minimize surface absorption of electrons in order to produce a modified SiPM device having the multi-pixel structure described herein but suitable for direct electron detection. More specifically, the technology steps used to create the antireflection layers (e.g., anti-reflective coating layer 32 in FIG. 4) normally included during the SiPM processing are eliminated and the passivation layer on the SiPM (e.g., SiO2 layer 35 in FIG. 4) is made very thin, on the order of 100 nm or less. Further, a bias voltage of 800-1000 volts can be placed on the device to assist SE collection. This will enable imaging at order-of-magnitude faster rates than prior semiconductor electron detectors, also known as simple photodiodes (200 nS per pixel for a modified SiPM vs. several μS per pixel for a simple photodiode; the slower imaging rates for simple photodiodes are due largely to their large size and accompanying capacitance, whereas APDs in SiPMs have small individual capacitances and therefore allow for very high imaging rates). While simple photodiodes have been used for direct electron detection in less demanding applications, they have output signals that are too slow to keep pace with the very fast scanning rates used in modern SEMs. Thus, the modified SiPM devices as just described may be used in place of the scintillator-SiPM coupled pair assemblies 24 in any of the embodiments described herein for direct electron detection rather than electron detection using a scintillator.

While for convenience the invention has been described herein in connection with and in the context of SEM 1, it should be understood that that is not mean to be limiting, and that the invention is applicable to all types of EMs (e.g., a transmission electron microscope (TEM)) and other charged particle beam devices/instruments such as, without limitation, other dual beam instruments as described elsewhere herein that may employ a focused ion beam in conjunction with an electron beam.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An X-ray detector, comprising:
   a housing;
   an X-ray sensing device provided within the housing, the X-ray sensing device being arranged to collect X-rays from a specimen; and
   an electron detector structured to detect a plurality of electrons ejected from the specimen in response to an electron beam impinging on the specimen, the electron detector being coupled to the housing and including one or more SiPMs, each of the one or more SiPMs being structured to generate a signal responsive to certain ones of the electrons, wherein the signal generated by each SiPM is based on an intensity of the certain ones of the electrons and is configured to be used to generate an image of the specimen, wherein the housing includes a front end structured to permit the X-rays to enter the housing, wherein the one or more SiPMs are positioned on an external surface of the front end of the housing, wherein the electron detector comprises one or more assemblies positioned on the external surface of the front end of the housing, each of the assemblies including one of the one or more SiPMs and a scintillator connected face-to-face to an active light sensing surface of the SiPM.

2. The X-ray detector according to claim 1, wherein the X-ray sensing device comprises a silicon drift detector.

3. An X-ray detector, comprising:
a housing;
an X-ray sensing device provided within the housing, the X-ray sensing device being arranged to collect X-rays from a specimen; and
an electron detector structured to detect a plurality of electrons ejected from the specimen in response to an electron beam impinging on the specimen, the electron detector being coupled to the housing and including one or more SiPMs, each of the one or more SiPMs being structured to generate a signal responsive to certain ones of the electrons, wherein the signal generated by each SiPM is based on an intensity of the certain ones of the electrons and is configured to be used to generate an image of the specimen, wherein the electron detector comprises one or more assemblies positioned within the housing, each of the assemblies including one of the one or more SiPMs and a scintillator directly connected to the one of the one or more SiPMs, wherein in each of the one or more assemblies the scintillator is structured to emit photons responsive to the certain ones of the electrons and the one of the one or more SiPMs is structured to generate the signal responsive to receipt of the photons.

4. The X-ray detector according to claim 1, further comprising an electron deflection device structured to direct the plurality of electrons away from the X-ray sensing device.

5. The X-ray detector according to claim 4, wherein the electron deflection device is positioned at an input end of the housing and the X-ray sensing device is spaced from the input end and the electron deflection device.

6. The X-ray detector according to claim 4, wherein the electron deflection device is a magnetic deflector structured to generate a magnetic field of sufficient strength to direct the plurality of electrons away from the X-ray sensing device.

7. The X-ray detector according to claim 1, wherein the electron detector is positioned adjacent to but not on a sensing axis of the X-ray sensing device.

8. The X-ray detector according to claim 4, wherein the electron deflection device is structured to be selectively and remotely turned on (active) and off (inactive).

9. An X-ray detector, comprising:
a housing;
an X-ray sensing device provided within the housing, the X-ray sensing device being arranged to collect X-rays from a specimen;
an electron detector structured to detect a plurality of electrons ejected from the specimen in response to an electron beam impinging on the specimen, the electron detector being coupled to the housing and including one or more SiPMs, each of the one or more SiPMs being structured to generate a signal responsive to certain ones of the electrons, wherein the signal generated by each SiPM is based on an intensity of the certain ones of the electrons and is configured to be used to generate an image of the specimen; and
an electron deflection device positioned at an input end of the housing, the X-ray sensing device being spaced from the input end and being behind the electron deflection device, wherein the electron detector is mounted within or adjacent to a center of the X-ray sensing device, and wherein the electron deflection device is structured to direct the plurality of electrons toward the electron detector and away from the X-ray sensing device.

10. An X-ray detector, comprising:
a housing;
an X-ray sensing device provided within the housing, the X-ray sensing device being arranged to collect X-rays from a specimen;
an electron detector structured to detect a plurality of electrons ejected from the specimen in response to an electron beam impinging on the specimen, the electron detector being coupled to the housing and including one or more SiPMs, each of the one or more SiPMs being structured to generate a signal responsive to certain ones of the electrons, wherein the signal generated by each SiPM is based on an intensity of the certain ones of the electrons and is configured to be used to generate an image of the specimen; and
an electron deflection device positioned at an input end of the housing, the X-ray sensing device being spaced from the input end and the electron deflection device, wherein the electron detector is mounted adjacent to an outer periphery of the X-ray sensing device, and wherein the electron deflection device is structured to direct the plurality of electrons toward the electron detector and away from the X-ray sensing device.

11. The X-ray detector according to claim 1, wherein the electron detector is positioned at an input end of the housing and comprises a substrate on which the one or more SiPMs are mounted, the substrate having a pass-through that is structured to allow X-rays to pass through the electron detector so that they can reach the X-ray sensing device, wherein the X-ray detector further comprises an electron deflection device positioned between the electron detector and the X-ray sensing device, wherein the electron deflection device is structured to direct the any electrons that pass through the electron detector away from the X-ray sensing device.

12. The X-ray detector according to claim 1, wherein a bias voltage is applied near the electron detector to accelerate electrons having lower energy than the bias voltage toward the electron detector.

13. An electron microscope including the X-ray detector according to claim 1.

14. The electron microscope according to claim 13, wherein the housing includes a front end structured to permit the X-rays to enter the housing, wherein the one or more SiPMs are positioned on an external surface of the front end of the housing, wherein the electron microscope includes an electron column along which an electron beam is directed, and wherein the housing is positioned such that a longitudinal axis of the housing is not parallel to the longitudinal axis of the electron column.

15. A method of detecting electrons and X-rays using an X-ray detector including a housing and an X-ray sensing device provided within the housing, the method comprising:
detecting one or more X-rays that enter the housing using the X-ray sensing device; and
detecting a plurality of electrons using an electron detector coupled to the housing, the electron detector including one or more SiPMs, the plurality of electrons being detected for use in generating an image of a specimen using electron imaging, the plurality of electrons being ejected from the specimen in response to an electron beam impinging on the specimen, wherein the housing includes a front end structured to permit the X-rays to enter the housing, wherein the one or more SiPMs are positioned on an external surface of the front end of the housing, and wherein the electron detector comprises one or more assemblies positioned on the external surface of the front end of the housing, each of the assemblies including one of the one or more SiPMs and a scintillator connected face-to-face to an active light sensing surface of the SiPM.

16. The method according to claim 15, wherein the X-ray sensing device comprises a silicon drift detector.

17. A method of detecting electrons and X-rays using an X-ray detector including a housing and an X-ray sensing device provided within the housing, the method comprising:
   detecting one or more X-rays that enter the housing using the X-ray sensing device; and
   detecting a plurality of electrons using an electron detector coupled to the housing, the electron detector including one or more SiPMs, the plurality of electrons being detected for use in generating an image of a specimen using electron imaging, the plurality of electrons being ejected from the specimen in response to an electron beam impinging on the specimen, wherein the electron detector comprises one or more assemblies positioned within the housing, each of the assemblies including one of the one or more SiPMs and a scintillator connected face-to-face to an active light sensing surface of the SiPM, wherein in each of the one or more assemblies the scintillator is structured to emit photons responsive to certain ones of the plurality of electrons and the one of the one or more SiPMs is structured to generate a signal responsive to receipt of the photons.

18. The method according to claim 15, further comprising deflecting the plurality of electrons away from the X-ray sensing device.

19. The X-ray detector according to claim 1, wherein the housing is separate from an electron column and a sample chamber of a charged particle beam device, the housing having an axis, wherein the X-ray sensing device is provided along the axis, wherein the housing is structured to be coupled to the electron column or the sample chamber of the charged particle beam device in a manner wherein the X-ray sensing device is arranged to collect the X-rays from the specimen when the specimen is positioned in the sample chamber, the electron detector being coupled to the housing on or near the axis such that a first line of sight to the one or more SiPMs from a point at which the electron beam impinges on the sample is similar to a second line of sight to the X-ray sensing device from the point at which the electron beam impinges on the sample such that X-ray and Backscattered electron images will show similar parallax and shadowing effects.

20. An X-ray detector, comprising:
   a housing separate from an electron column and a sample chamber of a charged particle beam device, the housing having a longitudinal axis;
   an X-ray sensing device provided within the housing along the longitudinal axis, wherein the housing is structured to provide a first line of sight to the X-ray sensing device along the longitudinal axis from outside the housing, wherein the housing is structured to be coupled to the electron column or the sample chamber of the charged particle beam device in a manner wherein the X-ray sensing device is arranged to collect X-rays from a sample positioned in the sample chamber along the first line of sight; and
   an electron detector structured to detect a plurality of electrons ejected from the sample in response to an electron beam impinging on the sample, the electron detector being coupled to the housing on or near the longitudinal axis in a manner that provides a second line of sight to the electron detector from a point at which the electron beam impinges on the sample such that the second line of sight to the electron detector is similar to the first line of sight to the X-ray sensing device such that X-ray and Backscattered electron images will show similar parallax and shadowing effects.

21. The X-ray detector according to claim 20, wherein the X-ray sensing device comprises a silicon drift detector.

22. The X-ray detector according to claim 20, wherein the housing includes a front end structured to permit X-rays to enter the housing, wherein the electron detector is positioned on an external surface of the front end of the housing.

23. The X-ray detector according to claim 22, wherein the electron detector comprises one or more assemblies positioned on the external surface of the front end of the housing, each of the assemblies including one or more SiPMs each having a scintillator directly connected thereto.

24. The X-ray detector according to claim 20, wherein the electron detector comprises one or more assemblies positioned within the housing.

25. The X-ray detector according to claim 20, further comprising an electron deflection device structured to direct the plurality of electrons away from the X-ray sensing device.

26. The X-ray detector according to claim 25, wherein the electron deflection device is positioned at an input end of the housing and the X-ray sensing device is spaced from the input end and the electron deflection device.

27. The X-ray detector according to claim 25, wherein the electron deflection device is a magnetic deflector structured to generate a magnetic field of sufficient strength to direct the plurality of electrons away from the X-ray sensing device.

28. The X-ray detector according to claim 20, wherein the electron detector is positioned adjacent to but not on a sensing axis of the X-ray sensing device.

29. The X-ray detector according to claim 25, wherein the electron deflection device is structured to be selectively and remotely turned on (active) and off (inactive).

30. The X-ray detector according to claim 20, further comprising an electron deflection device positioned at an input end of the housing, the X-ray sensing device being spaced from the input end and being behind the electron deflection device, wherein the electron detector is mounted within or adjacent to a center of the X-ray sensing device, and wherein the electron deflection device is structured to direct the plurality of electrons toward the electron detector and away from the X-ray sensing device.

31. The X-ray detector according to claim 20, further comprising an electron deflection device positioned at an input end of the housing, the X-ray sensing device being spaced from the input end and the electron deflection device, wherein the electron detector is mounted adjacent to an outer periphery of the X-ray sensing device, and wherein the electron deflection device is structured to direct the plurality of electrons toward the electron detector and away from the X-ray sensing device.

32. The X-ray detector according to claim 20, wherein the electron detector is positioned at an input end of the housing and comprises a substrate having a pass-through that is structured to allow X-rays to pass through the electron detector so that they can reach the X-ray sensing device, wherein the X-ray detector further comprises an electron deflection device positioned between the electron detector and the X-ray sensing device, wherein the electron deflection device is structured to direct the any electrons that pass through the electron detector away from the X-ray sensing device.

33. The X-ray detector according to claim 20, wherein a bias voltage is applied near the electron detector to accelerate electrons having lower energy than the bias voltage toward the electron detector.

34. An electron microscope including the X-ray detector according to claim 20, wherein the electron beam is directed in a first direction.

35. The electron microscope according to claim 34, wherein the housing includes a front end structured to permit X-rays to enter the housing, wherein the electron detector comprises one or more assemblies positioned on an external surface of the front end of the housing, each of the assemblies including one or more SiPMs each having a scintillator directly connected thereto, wherein the one or more SiPMs are positioned on an external surface of the front end of the housing, wherein the electron microscope includes an electron column along which an electron beam is directed, and wherein the housing is positioned such that a longitudinal axis of the housing is not parallel to the longitudinal axis of the electron column.

36. A method of detecting electrons and X-rays using an X-ray detector including a housing separate from an electron column and a sample chamber of a charged particle beam device, the housing having an axis, the method comprising:
directing an electron beam toward a sample positioned in the sample chamber in a first direction such that the electron beam impinges on the sample;
detecting one or more X-rays from the sample that enter the housing using an X-ray sensing device provided within the housing along the axis, wherein the housing is coupled to the electron column or the sample chamber of the charged particle beam device in a manner wherein the X-ray sensing device is arranged to collect the one or more X-rays; and
detecting a plurality of electrons ejected from the sample in response to the electron beam impinging on the sample using an electron detector, the electron detector being coupled to the housing on or near the axis and such that a first line of sight to the electron detector from a point at which the electron beam impinges on the sample is similar to a second line of sight to the X-ray sensing device from the point at which the electron beam impinges on the sample such that X-ray and Backscattered electron images will show similar parallax and shadowing effects, wherein the first line of sight and the second line of sight are transverse to the first direction.

37. The method according to claim 36, wherein the X-ray sensing device comprises a silicon drift detector.

38. The method according to claim 36, wherein the housing includes a front end structured to permit the X-rays to enter the housing, wherein the electron detector is positioned on an external surface of the front end of the housing.

39. The method according to claim 36, wherein the electron detector comprises one or more assemblies positioned on the external surface of the front end of the housing, each of the assemblies including one or more SiPMs each having a scintillator directly connected thereto.

40. The method according to claim 36, further comprising deflecting the plurality of electrons away from the X-ray sensing device.

* * * * *